(12) United States Patent
Takenaka et al.

(10) Patent No.: US 9,804,189 B2
(45) Date of Patent: Oct. 31, 2017

(54) UPPER BODY MOTION MEASUREMENT SYSTEM AND UPPER BODY MOTION MEASUREMENT METHOD

(71) Applicants: HONDA MOTOR CO., LTD., Tokyo (JP); KYOTO UNIVERSITY, Kyoto-shi, Kyoto (JP)

(72) Inventors: Toru Takenaka, Saitama (JP); Yasushi Ikeuchi, Saitama (JP); Yosuke Nagata, Saitama (JP); Koji Ohata, Kyoto (JP)

(73) Assignees: HONDA MOTOR CO., LTD., Tokyo (JP); KYOTO UNIVERSITY, Kyoto (JP)

( * ) Notice: Subject to any disclaimer, the term of this patent is extended or adjusted under 35 U.S.C. 154(b) by 328 days.

(21) Appl. No.: 14/668,217

(22) Filed: Mar. 25, 2015

(65) Prior Publication Data

US 2015/0276793 A1    Oct. 1, 2015

(30) Foreign Application Priority Data

Mar. 26, 2014    (JP) .................................. 2014-064658

(51) Int. Cl.
*A61B 5/00*      (2006.01)
*G01P 15/18*     (2013.01)
*G01C 21/16*     (2006.01)
*A61B 5/107*     (2006.01)
*A61B 5/11*      (2006.01)

(52) U.S. Cl.
CPC ............ *G01P 15/18* (2013.01); *A61B 5/1071* (2013.01); *A61B 5/1121* (2013.01); *G01C 21/16* (2013.01); *A61B 5/112* (2013.01); *A61B 5/1116* (2013.01)

(58) Field of Classification Search
CPC ....... A61B 5/11; A61B 5/1112; A61B 5/1116; A61B 5/112; A61B 5/1121; A61B 5/1123
See application file for complete search history.

(56) References Cited

U.S. PATENT DOCUMENTS

| 5,919,149 A * | 7/1999 | Allum .................... A61B 5/1116 |
| | | 600/595 |
| 6,063,046 A * | 5/2000 | Allum ................... A61B 5/1036 |
| | | 600/595 |
| 8,626,472 B2 * | 1/2014 | Solinsky ................. A61B 5/112 |
| | | 235/105 |
| 8,821,305 B2 * | 9/2014 | Cusey ................... A61B 5/1124 |
| | | 340/539.22 |

(Continued)

FOREIGN PATENT DOCUMENTS

JP    2012-065723 A    4/2012

*Primary Examiner* — Max Hindenburg
(74) *Attorney, Agent, or Firm* — Squire Patton Boggs (US) LLP

(57) ABSTRACT

An upper body motion measurement system 1 has a plurality of inertia sensor units 2, each of which incorporating an angular velocity sensor 4 and an acceleration sensor 5. The plurality of the inertia sensor units 2 is attached to places that are different from each other on the upper body of a subject P. Based on the detection outputs of the angular velocity sensor 4 and the acceleration sensor 5, the attitude of each of the inertia sensor units 2 is estimated, and the acceleration thereof is further estimated. The angular acceleration of the upper body of the subject P is estimated based on the estimated accelerations of the plurality of the inertia sensor units 2.

11 Claims, 9 Drawing Sheets

(56) References Cited

U.S. PATENT DOCUMENTS

| | | | |
|---|---|---|---|
| 8,868,369 B2* | 10/2014 | Esser | A61B 5/112 |
| | | | 702/104 |
| 9,119,569 B2* | 9/2015 | Chen | A61B 5/11 |
| 9,597,015 B2* | 3/2017 | McNames | A61B 5/1071 |

* cited by examiner

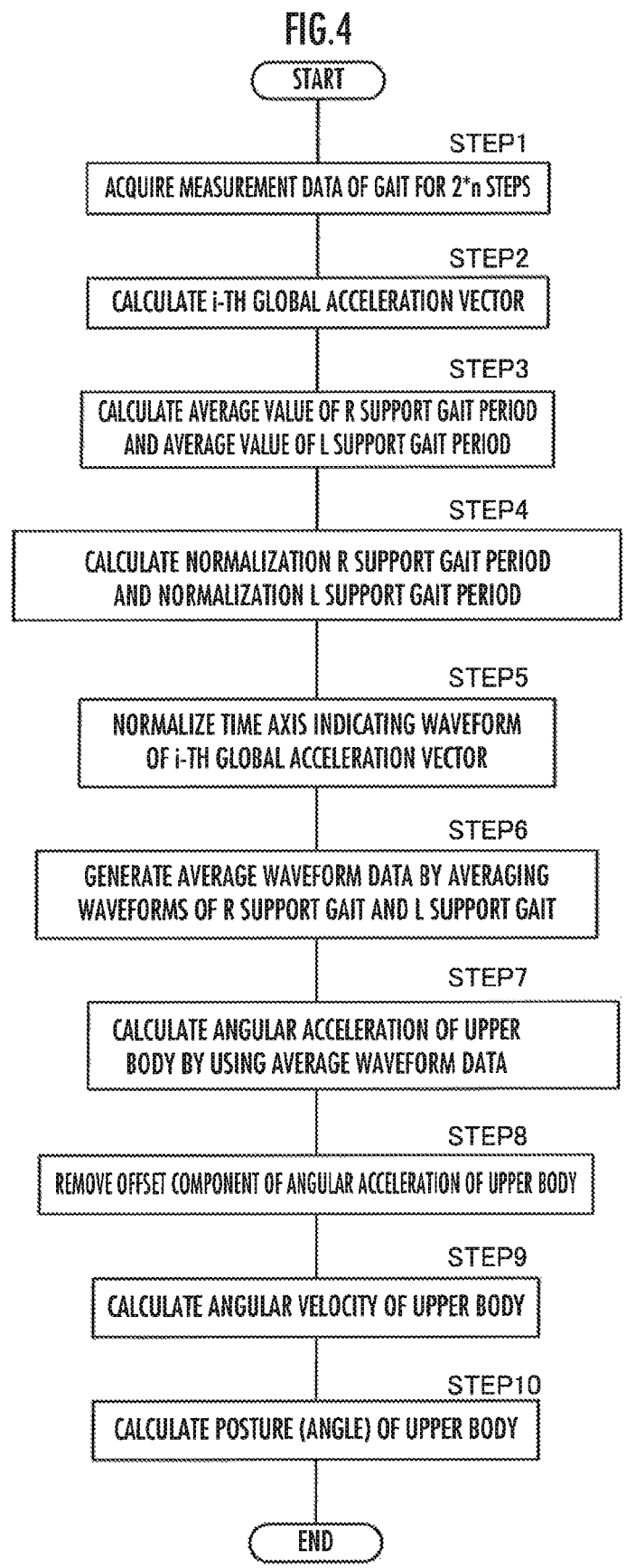

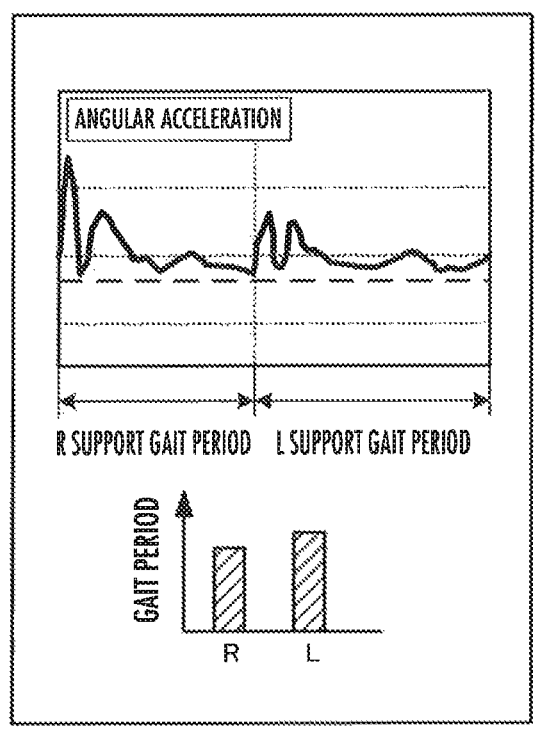

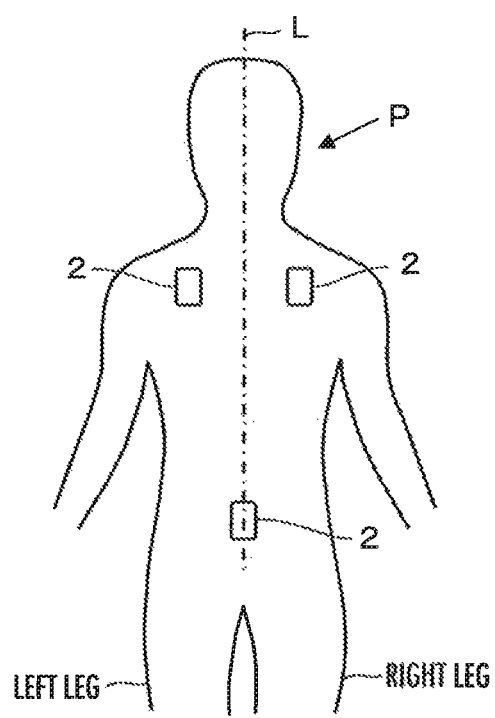

UPPER BODY MOTION MEASUREMENT SYSTEM AND UPPER BODY MOTION MEASUREMENT METHOD

BACKGROUND OF THE INVENTION

Field of the Invention

The present invention relates to a system and a method for estimating the change in the posture of the upper body of a person (subject).

Description of the Related Art

Hitherto, in order to grasp the walking state of a person, the posture of a predetermined part of a walking person, or a change or the like of the posture has generally been measured using an angular velocity sensor, such as a gyro sensor.

For example, Japanese Patent Application Laid-Open No. 2012-65723 (hereinafter referred to as Patent Document 1) describes a technique in which gyro sensors are attached to the waist and the thigh, the crus and the foot of each leg of a walker, and the joint angles of a hip joint, a knee joint, and an ankle joint are measured using the detection values of the gyro sensors.

In the meantime, according to various experiments and studies carried out by the inventors of the present application, the change in the posture of the upper body of a walking person, especially the change in the posture of the upper body in a pitch direction or a roll direction is markedly influenced by the motions of the legs of the walking person.

Further, especially the angular acceleration of the upper body is closely connected with the state of a floor reaction force acting on the walking person.

Therefore, observing the change in the posture of the upper body, including the angular acceleration, of the upper body of the walking person is highly necessary for grasping or assessing the walking state (e.g. the motional balance of right and left legs or the state of a leg motion recovered by rehabilitation) of a person.

In this case, angular velocity sensors, such as gyro sensors, could be attached to the upper body of a person, so that the change in the posture of the upper body could be observed based on the detection values of the angular velocities indicated by the angular velocity sensors. Further, in this case, as with the gyro sensor on the waist described in Patent Document 1, an angular velocity sensor could be attached to the upper body of a person through a fixing plate, such as a wide belt.

However, according to the technique in which an angular velocity sensor is attached to the upper body of a person through a fixing plate, such as a wide belt, as described above, the fixing plate is placed on a relatively large contact surface of the upper body of a person. This tends to cause the person discomfort or the feeling of an attached foreign object.

Further, in some cases, the discomfort, the feeling of an attached foreign object or the weight of the fixing plate inconveniently causes the walking form of a person to be different from his/her normal walking form without the fixing plate attached. This makes it impossible to properly assess the walking state of the person with high reliability.

To avoid the aforesaid inconvenience, the contact area occupied by the angular velocity sensor attached to the upper body of the person could be minimized.

This, however, would make it difficult to cause the attitude of the angular velocity sensor to accurately and stably follow the posture of the upper body of the person. Hence, the change in the attitude of the angular velocity sensor tends to deviate from the actual change in the posture of the upper body. As a result, it becomes difficult to observe the posture change of the upper body of the person with high reliability.

Further, if, for example, the angular acceleration of the upper body of a person is to be measured using an angular velocity sensor attached to the upper body, then it is necessary to carry out calculation for differentiating the detection values of the angular velocity obtained by the angular velocity sensor. Therefore, the measurement values of the angular velocity of the upper body are susceptible to the influence of noise components contained in the detection values of the angular velocity. This is inconveniently prone to result in deteriorated measurement accuracy of the angular acceleration of the upper body.

SUMMARY OF THE INVENTION

The present invention has been made in view of the background described above and an object of the invention is to provide a system and a method that allow the change in the posture of the upper body of a person (subject) to be properly measured.

To this end, an upper body motion measurement system in accordance with the present invention includes: a plurality of inertia sensor units, each of which has a set of an angular velocity sensor that detects an angular velocity and an acceleration sensor that detects an acceleration and which are attached to places that are different from each other on an upper body of a subject;

a sensor unit attitude estimating unit which estimates the attitude of each of the inertia sensor units in a motion environment of the subject based on a detection value of an angular velocity and a detection value of an acceleration indicated by detection outputs of an angular velocity sensor and an acceleration sensor of each of the inertia sensor units attached to the upper body of the subject;

a sensor unit acceleration estimating unit which estimates the acceleration of each of the inertia sensor units observed in a global coordinate system set in the motion environment of the subject based on a detection value of an acceleration indicated by a detection output of the acceleration sensor of each of the inertia sensor units attached to the upper body of the subject, and the attitude of each of the inertia sensor units estimated by the sensor unit attitude estimating unit; and an upper body angular acceleration estimating unit which estimates an angular acceleration of the upper body of the subject observed in the global coordinate system by linearly combining accelerations estimated by the sensor unit acceleration estimating unit on each of at least two inertia sensor units among the plurality of inertia sensor units (a first aspect of the invention).

In the present invention, the angular velocity detected by the angular velocity sensor of each of the inertia sensor units is more specifically a spatial (three-dimensional space) angular velocity vector. Similarly, the acceleration detected by the acceleration sensor of each of the inertia sensor units is more specifically a spatial (three-dimensional space) acceleration vector.

According to the first aspect of the invention described above, the attitude (spatial attitude) of each of the inertia sensor units in the motion environment of the subject wearing the plurality of inertia sensor units is estimated by the sensor unit attitude estimating unit.

Here, each of the inertia sensor units is provided with a set of the angular velocity sensor and the acceleration sensor. This makes it possible to estimate the attitude of each of the inertia sensor units based on a detection value of the angular velocity and a detection value of the acceleration indicated by the detection outputs of the angular velocity sensor and the acceleration sensor of the inertia sensor unit. As the arithmetic processing for the estimation, publicly known arithmetic processing, e.g. strap-down calculation, may be adopted.

Further, the acceleration (translational acceleration) of each inertia sensor unit observed in the global coordinate system set in the motion environment of the subject is estimated by the sensor unit acceleration estimating unit.

In this case, a detection value of the acceleration indicated by a detection output of the acceleration sensor of each of the inertia sensor units is a translational acceleration that can be represented by a local coordinate system fixed with respect to the acceleration sensor or the inertia sensor unit. Further, the attitude of each inertia sensor unit in the motion environment of the subject is estimated by the sensor unit attitude estimating unit.

Thus, for each inertia sensor unit, the acceleration (translational acceleration) of each inertia sensor unit observed in the global coordinate system can be estimated based on the detection value of the acceleration indicated by the detection output of the acceleration sensor of each inertia sensor unit and the attitude of the inertia sensor unit estimated by the sensor unit attitude estimating unit.

Further, the angular acceleration of the upper body of the subject is estimated by the upper body angular acceleration estimating unit.

Here, if an angular acceleration is generated due to a change in the posture of the upper body, then the accelerations (translational accelerations) of parts of the upper body that are apart from each other are generally different from each other even if the angular acceleration remains constant. For example, the acceleration of a part that is farther from the vicinity around the center of rotation of the upper body posture is higher than the acceleration of a part closer to the center of rotation.

Therefore, whenever the angular acceleration of the upper body changes due to a motion of the upper body of the subject at the time of walking or the like, the set of the acceleration values of each of the plurality of inertia sensor units attached to different places of the upper body of the subject changes.

In this case, even if the places of the upper body of the subject where the inertia sensor units are attached are local, the inertia sensor units can be attached to the upper body of the subject such that the acceleration (the translational acceleration) of the inertia sensor units will closely follow the acceleration of the parts of the upper body at which the inertia sensor units are installed.

Accordingly, based on the set of the accelerations estimated by the sensor unit acceleration estimating unit on each of the plurality of inertia sensor units, the angular acceleration of the upper body of the subject observed in the global coordinate system is estimated by the upper body angular acceleration estimating unit, thereby making it possible to obtain an estimated value that closely follows an actual angular acceleration.

Further, the places of the upper body of the subject to which the inertia sensor units are attached can be localized, so that the inertia sensor units can be attached to the upper body of the subject without causing a feeling of strangeness or discomfort to the subject. This prevents the occurrence of the difference in motion of the subject whether or not the subject is wearing the plurality of the inertia sensor units. Therefore, the angular acceleration of the upper body can be measured on a normal motion of the subject not wearing the plurality of the inertia sensor units.

According to the first aspect of the invention, therefore, the change in the posture of the upper body of a person (subject) can be properly measured.

In the present invention, the upper body angular acceleration estimating unit is capable of calculating the estimated value of the angular acceleration of the upper body of the subject by, for example, linearly combining the estimated values of the accelerations of the plurality of the inertia sensor units. In this case, as the coefficient value of the linear combination, a value set according to the distance between the inertia sensor units or the positional relationship therebetween or an experimentally set value or the like may be used.

Further, the angular acceleration estimated by the upper body angular acceleration estimating unit may be a spatial angular acceleration vector or an angular acceleration in particular one or two directions.

In the first aspect of the invention described above, preferably, the plurality of the inertia sensor units includes at least two inertia sensor units attached to the upper body with an interval provided in a vertical direction of the upper body along a trunk axis of the subject, and the angular acceleration estimated by the upper body angular acceleration estimating unit includes at least one of the angular acceleration of the upper body in the roll direction of the subject and the angular acceleration in the pitch direction of the subject (a second aspect of the invention).

In the present invention, the roll direction, the pitch direction, and a yaw direction mean the direction about the axis in substantially the longitudinal direction (roll axis direction) of the subject, the direction about the axis in substantially the lateral direction (pitch axis direction) of the subject, and the direction about the axis in substantially the vertical direction (yaw axis direction) of the subject, respectively, when the subject wearing the plurality of the inertia sensor units is standing upright.

According to the second aspect of the invention, the two inertia sensor units are attached to the upper body with an interval provided in the vertical direction of the upper body along the trunk axis of the upper body of the subject. Hence, the set of the accelerations (the accelerations observed in the global coordinate system) of the two inertia sensor units exhibits high correlativity to the angular acceleration of the upper body in the roll direction of the subject and the angular acceleration in the pitch direction of the subject.

More specifically, of the accelerations of the two inertia sensor units, mainly the set of the values of the accelerations in the pitch axis direction (substantially lateral direction) of the subject has higher correlativity to the angular acceleration in the roll direction of the upper body of the subject.

Further, of the accelerations of the two inertia sensor units, mainly the set of the values of the accelerations in the roll axis direction (substantially longitudinal direction) of the subject has higher correlativity to the angular acceleration in the pitch direction of the upper body of the subject.

According to the second aspect of the invention, therefore, one or both of the angular accelerations in the pitch direction and the roll direction of a subject can be estimated with high reliability. This makes it possible to obtain highly useful measurement data (the estimated values of the angular accelerations) in analyzing or assessing the state of a motion, such as a walking motion, of the subject.

In the second aspect of the invention, preferably, an upper inertia sensor unit of the two inertia sensor units is attached to the upper body of the subject at a location on an upper side from the boundary between a thoracic vertebra and a lumbar vertebra of the subject, and a lower inertia sensor unit of the two inertia sensor units is attached to the upper body of the subject at a location on a lower side from the boundary between the thoracic vertebra and the lumbar vertebra of the subject (a third aspect of the invention).

Here, in the upper body of the subject, the location on the upper side from the boundary between the thoracic vertebra and the lumbar vertebra of the subject is a location under which ribs are disposed. Hence, the location has a relatively high rigidity in the upper body.

Further, the location on the lower side from the boundary corresponds to a location in the vicinity of the center of rotation of the posture in the pitch direction or the roll direction of the upper body of the subject.

Thus, according to the third aspect of the invention, the angular acceleration in one or both of the pitch direction and the roll direction of the subject can be estimated with even higher reliability.

Further, in the first to the third aspects of the invention, preferably, the acceleration of each of the inertia sensor units observed in the global coordinate system or the angular acceleration of the upper body of the subject observed in the global coordinate system is defined as a target state amount, and the sensor unit acceleration estimating unit or the upper body angular acceleration estimating unit is configured to carry out basic estimated value generation processing for generating a time series of estimated values of the target state amount in a walking motion and average waveform data generation processing for generating average waveform data of the target state amount of a two-step gait in the walking motion in the case where the subject wearing the plurality of inertia sensor units on his/her upper body performs a walking motion, and the average waveform data generation processing is configured to transform in scale the waveform data, which is indicated by the time series of the estimated values of the target state amount generated by the basic estimated value generation processing for each of an n number (n: an integer of 2 or more) of two-step gaits included in the walking motion of the subject, in the direction of a time axis thereby to generate normalized waveform data obtained by normalizing a time width of a period of the two-step gait and further configured to generate average waveform data of an n number of pieces of the normalized waveform data for each of the n number of the two-step gaits as the average waveform data (a fourth aspect of the invention).

In the fourth aspect of the invention, when the sensor unit acceleration estimating unit carries out the basic estimated value generation processing and the average waveform data generation processing, which are related to the acceleration of each of the inertia sensor units as the target state amount, the basic estimated value generation processing, more specifically, calculates, for each of the inertia sensor units, the time series of the estimated value of the target state amount (the acceleration of each of the inertia sensor units) in the walking motion based on a detection value of the acceleration indicated by a detection output of the acceleration sensor of the inertia sensor unit and an attitude of the inertia sensor unit estimated by the sensor unit attitude estimating unit.

Further, when the upper body posture angular acceleration estimating unit carries out the basic estimated value generation processing and the average waveform data generation processing related to the angular acceleration of the upper body of the subject as the target state amount, the basic estimated value generation processing, more specifically, calculates, for each of the plurality of inertia sensor units, the time series of the estimated value of the target state amount (the angular acceleration of the upper body) in the walking motion based on a set of accelerations estimated by the sensor unit acceleration estimating unit.

Here, to analyze or assess the motion of the upper body during a walking motion of the subject, it is considered to be desirable to obtain the waveform data of an average upper body motion (acceleration, angular acceleration and the like) during the period of the gait for two steps in the walking motion composed of a plurality of steps of the subject (i.e. the gait for one period in the repetition of the walking motion).

In the fourth aspect of the invention, therefore, the sensor unit acceleration estimating unit or the upper body angular acceleration estimating unit carries out the average waveform data generation processing in addition to the basic estimated value generation processing so as to obtain continuous waveform data of the target state amount.

In this case, the time width of the period of each of the n number of (a plurality of) the two-step gaits included in the walking motion of the subject generally differs from each other for each of the n number of (the plurality of) the two-step gaits even in the case of a normal walking motion.

Therefore, in the average waveform data generation processing, for each of the n number of (the plurality of) the two-step gaits, the normalized waveform data obtained by normalizing the time width of the period of the two-step gait is generated and then the average waveform data is generated.

Normalizing the time width of the period of the two-step gait means to set the time width of each of the n number of the two-step gaits to a same predetermined value (fixed value).

Thus, the average waveform data can be properly generated as the average waveform data of the target state amount during the period of the two-step gait in the walking motion of the subject.

Further, using the average waveform data generated as described above makes it possible to properly analyze or assess the walking state of the subject with high reliability.

Supplementarily, in the present invention, the values (instantaneous values) of the target state amounts indicated by the average waveform data are regarded as the estimated values of the target state amounts.

Accordingly, when the sensor unit acceleration estimating unit carries out the basic estimated value generation processing and the average waveform data generation processing related to the acceleration of each of the inertia sensor units as the target state amount, the value of the acceleration of the inertia sensor unit indicated by the average waveform data for each inertia sensor unit has a meaning as the acceleration estimated by the sensor unit acceleration estimating unit.

In this case, the upper body angular acceleration estimating unit is capable of estimating the angular acceleration (an instantaneous value or the time series thereof) of the subject in the period of the two-step gait by using the value (estimated value) of the acceleration indicated by the average waveform data related to each of the plurality of the inertia sensor units.

In the fourth aspect of the invention, processing for generating the normalized waveform data in the average waveform data generation processing is preferably configured to generate the normalized waveform data such that a ratio between a time width of a one-step period of a right leg of the subject and a time width of a one-step period of a left leg of the subject in the normalized waveform data coincides with a ratio between an average value of an actual time width of the one-step period of the right leg in an n number of two-step gaits included in the walking motion of the subject and an average value of an actual time width of the one-step period of the left leg in the n number of two-step gaits (a fifth aspect of the invention).

The one-step period of the right leg of the subject means the period in which the right leg acts as a supporting leg (or a free leg), and the one-step period of the left leg of the subject means the period in which the left leg acts as the supporting leg (or the free leg). In this case, for the sake of convenience, in a double stance phase, the leg that leaves a floor immediately after the double stance phase, for example, may be defined as the free leg, and the other leg may be defined as the supporting leg. Alternatively, in reverse, the leg that leaves the floor immediately after the double stance phase may be defined as the supporting leg, and the other leg may be defined as the free leg.

According to the fifth aspect of the invention described above, the same timing of switching between the one-step period of the right leg and the one-step period of the left leg in each piece of the n number of the normalized waveform data corresponding to each of the n number of two-step gaits (the timing within the period of the two-step gait) applies to any of the n number of pieces of the normalized waveform data.

Thus, the average waveform data of a target state amount in the vicinity of the switching timing can be properly obtained with high reliability. Further, the average waveform data makes it possible to properly distinguish or compare the waveform of a target state amount in the one-step period of the right leg and the waveform of a target state amount in the one-step period of the left leg.

In the fourth aspect or the fifth aspect of the invention, preferably, the sensor unit acceleration estimating unit or the upper body angular acceleration estimating unit, which carries out the average waveform data generation processing, is configured to further carry out offset component removal processing for removing an offset component from the average waveform data generated by the average waveform data generation processing, and the offset component removal processing is configured to remove the offset component such that a condition is satisfied, in which an average value in the period of the two-step gait of the value of the target state amount indicated by average waveform data after the offset component is removed becomes zero (a sixth aspect of the invention).

More specifically, the average waveform data (average waveform data of the n number of pieces of the normalized waveform data corresponding to each of the n number of the two-step gaits) generally includes an offset component due to a drift or the like of a detection output of the angular velocity sensor or the acceleration sensor of each of the inertia sensor units.

Meanwhile, in a normal walking motion of the subject or a walking motion close thereto, the average value of actual values of the target state amount in the two-step gait period is zero or approximately zero.

Thus, an offset component can be properly removed from the average waveform data. This permits enhanced matching between the polarity of a value of the target state amount in the average waveform data and an actual polarity. Hence, the reliability of the average waveform data can be further enhanced.

In the fourth to the sixth aspects of the invention, ideally generating the average waveform data requires accurate recognition of the switching timing for each step (the timing of switching from one step of either the right leg or the left leg to one step of the other leg) in the walking motion of the subject.

In this case, such recognition can be achieved by, for example, providing the soles of both legs with ground contact sensors that detect the landing/leaving of each of the both legs of the subject on/from a floor.

Meanwhile, according to various experiments and studies carried out by the inventors of the present application, at least one inertia sensor unit among the plurality of inertia sensor units can be disposed such that the acceleration of the inertia sensor unit (e.g. the inertia sensor unit on the lower side in the second aspect or the third aspect of the invention) exhibits a relatively marked change in the vicinity of the switching timing for each step.

Therefore, in the fourth to the sixth aspect of the invention, the sensor unit acceleration estimating unit or the upper body angular acceleration estimating unit, which carries out the average waveform data generation processing, may be configured to recognize a switching timing for each step in a walking motion of the subject based on a detection value of acceleration indicated by a detection output of an acceleration sensor of at least one inertia sensor unit among the plurality of the inertia sensor units or a change in acceleration estimated by the sensor unit acceleration estimating unit on at least the one inertia sensor unit (a seventh aspect of the invention).

According to the seventh aspect of the invention, the switching timing for each step in the walking motion of the subject can be properly recognized without providing the foregoing ground contact sensors or the like. This allows highly reliable average waveform data to be obtained.

Further, in the fourth to the seventh aspects of the invention, the angular velocity of the upper body can be estimated using the time series of the estimated value of the angular acceleration of the upper body of the subject. In this case, the following configuration is desirably adopted.

If the sensor unit acceleration estimating unit is configured to generate the average waveform data related to the acceleration of each of the inertia sensor units, then the upper body angular acceleration estimating unit is configured to generate angular acceleration waveform data composed of the time series of an estimated value of the angular acceleration of the upper body of the subject in the period of the two-step gait by using an estimated value of the acceleration of each of the inertia sensor units indicated by the average waveform data generated by the sensor unit acceleration estimating unit on each of at least two inertia sensor units.

In addition, in this case, preferably, an upper body angular velocity estimating unit that calculates an estimated value of the angular velocity of the upper body of the subject by integrating an estimated value of angular acceleration indicated by the angular acceleration waveform data generated by the upper body angular acceleration estimating unit is further provided, and the upper body angular velocity estimating unit is configured to calculate an estimated value of an angular velocity of the upper body of the subject such that a condition is satisfied, in which an average value of an estimated value of the angular velocity of the upper body of the subject in the period of the two-step gait is zero (an eighth aspect of the invention).

Alternatively, if the upper body angular acceleration estimating unit is configured to generate the average waveform data related to the angular acceleration of the upper body of the subject, then preferably, an upper body angular velocity estimating unit that calculates an estimated value of the angular velocity of the upper body of the subject by integrating an estimated value of angular acceleration indicated by the average waveform data generated by the upper body angular acceleration estimating unit is further provided, and the upper body angular velocity estimating unit is configured to calculate an estimated value of the angular velocity of the upper body of the subject such that a condition is satisfied, in which an average value of the estimated value of the angular velocity of the upper body of the subject in the period of the two-step gait is zero (a ninth aspect of the invention).

Here, in a normal walking motion of the subject or a walking motion close thereto, the average value of actual values of the angular velocity of the upper body of the subject in the two-step gait period is zero or approximately zero.

Accordingly, in the eighth or the ninth aspect of the invention, the upper body angular velocity estimating unit calculates the estimated value of the angular velocity of the upper body of the subject such that the condition is satisfied, in which the average value of the estimated value of the angular velocity of the upper body of the subject in the two-step gait period is zero.

Thus, the estimated value (instantaneous value or the time series thereof) of an average upper body angular velocity of the subject in the two-step gait period can be properly calculated with high reliability.

If the eighth or the ninth aspect of the invention described above is combined with the foregoing sixth aspect of the invention, then the average waveform data means the average waveform data from which the offset component has been removed.

Further, an upper body motion measurement method in accordance with the present invention includes: a first step of acquiring a detection output of each of an angular velocity sensor and an acceleration sensor of each of a plurality of inertia sensor units in a state in which the plurality of the inertia sensor units, each of which has a set of the angular velocity sensor that detects an angular velocity and the acceleration sensor that detects an acceleration, are attached to places that are different from each other on an upper body of a subject;

a second step of estimating an attitude of each of the inertia sensor units in a motion environment of the subject based on a detection value of an angular velocity and a detection value of an acceleration indicated by detection outputs of the angular velocity sensor and the acceleration sensor of each of the inertia sensor units acquired in the first step;

a third step of estimating an acceleration of each of the inertia sensor units observed in a global coordinate system set in a travel environment of the subject based on a detection value of an acceleration indicated by a detection output of the acceleration sensor of each of the inertia sensor units acquired in the first step, and the attitude of each of the inertia sensor units estimated in the second step on each of the inertia sensor units; and a fourth step of estimating an angular acceleration of the upper body of the subject observed in the global coordinate system based on a set of accelerations estimated in the third step on each of the plurality of the inertia sensor units (a tenth aspect of the invention).

According to the tenth aspect of the invention, the attitude (spatial attitude) of each of the inertia sensor units in the motion environment of the subject wearing the plurality of the inertia sensor units is estimated in the second step. The estimation processing is carried out in the same manner as with the processing carried out by the sensor unit attitude estimating unit in the first aspect of the invention.

Further, the acceleration (translational acceleration) of each of the inertia sensor units observed in the global coordinate system set in the travel environment of the subject is estimated in the third step. The estimation processing is carried out in the same manner as that of the processing carried out by the sensor unit acceleration estimating unit in the first aspect of the invention.

Further, in the fourth step, the angular acceleration of the upper body of the subject is estimated. The estimation processing is carried out in the same manner as that of the processing carried out by the upper body angular acceleration estimating unit in the first aspect of the invention.

Thus, based on the set of accelerations estimated on each of the plurality of the inertia sensor units, the angular acceleration of the upper body of the subject observed in the global coordinate system is estimated, thereby making it possible to obtain an estimated value that closely follows an actual angular acceleration.

Further, as with the first aspect of the invention, the places of the upper body of the subject to which the inertia sensor units are attached can be localized. This makes it possible to prevent the occurrence of the difference in motion of the subject whether or not the subject is wearing the plurality of the inertia sensor units. Therefore, the angular acceleration of the upper body can be measured on a normal motion of the subject not wearing the plurality of the inertia sensor units.

According to the tenth aspect of the invention, therefore, a change in the posture of the upper body of a person (subject) can be properly measured.

BRIEF DESCRIPTION OF THE DRAWINGS

FIG. 4 is a flowchart illustrating the processing carried out by a data acquisition device illustrated in FIG. 1;

FIG. 6 is a diagram illustrating a display example of data obtained in the embodiment;

FIG. 9 is a diagram illustrating another example of the layout of the inertia sensor units attached to the upper body of the subject;

DESCRIPTION OF THE PREFERRED EMBODIMENTS

First Embodiment

The following will describe a first embodiment of the present invention with reference to FIG. 1 to FIG. 7.

Figure 1A:
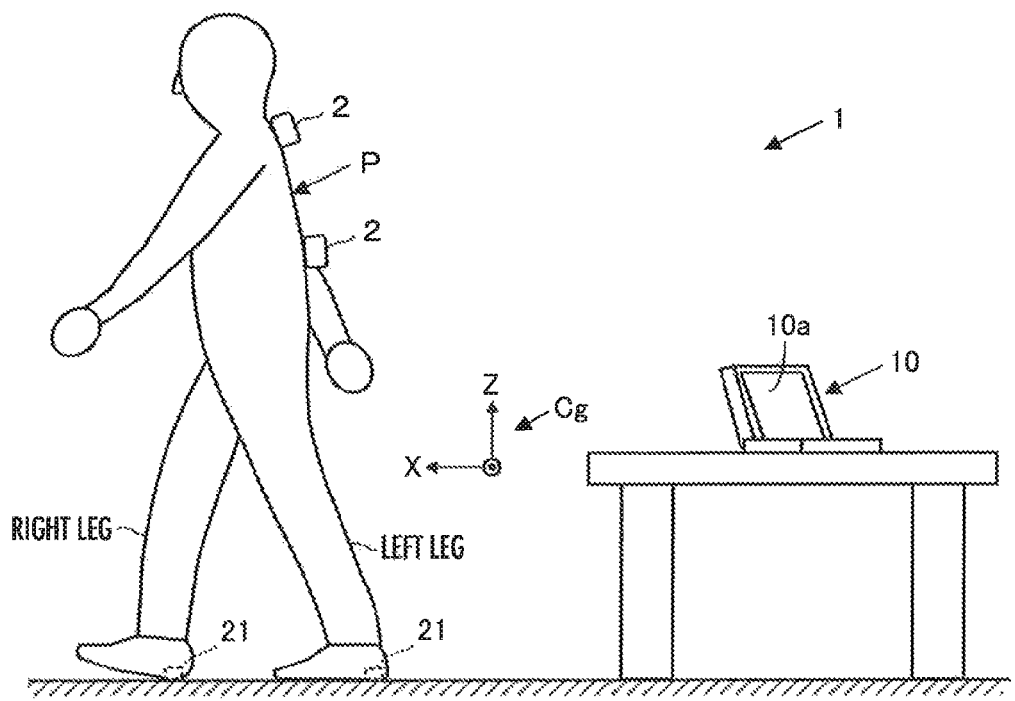
FIG. 1A is a diagram illustrating a general configuration of an upper body motion measurement system according to a first embodiment.
Figure 1B:
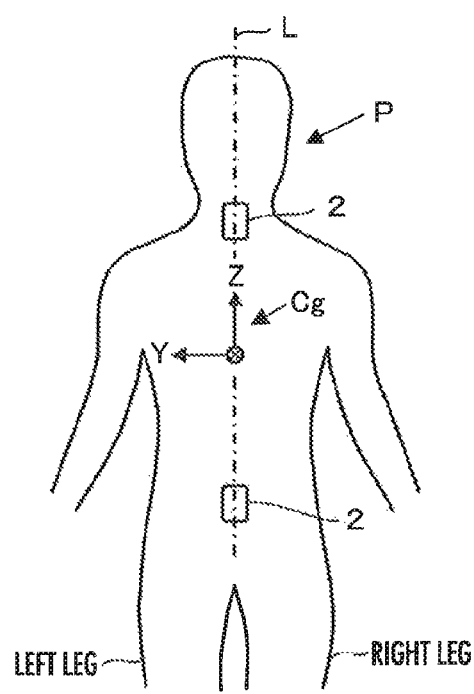
FIG. 1B is a diagram illustrating a layout of inertia sensor units attached to the upper body of a subject in the first embodiment.

Referring to FIG. 1A and FIG. 1B, an upper body motion measurement system 1 according to the present embodiment has two inertia sensor units 2, 2 attached to a subject P, and a data acquisition device 10 that mainly acquires measurement data through communication with the inertia sensor units 2, 2.

Figure 2:
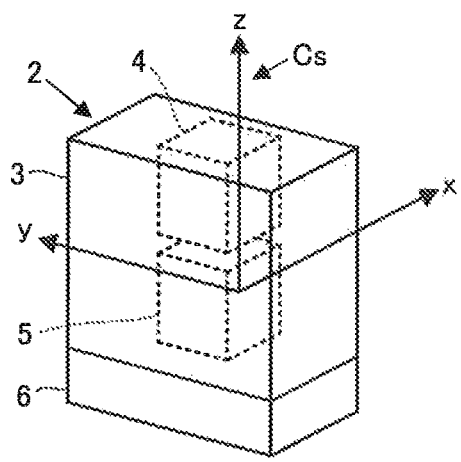
FIG. 2 is a perspective view illustrating the configuration of each of the inertia sensor units of the embodiment.

Each of the inertia sensor units 2 (hereinafter referred to simply as the sensor unit 2) includes an angular velocity sensor 4 and an acceleration sensor 5 housed in a chassis 3, and a circuit unit 6 having a communication function and the like, as illustrated in FIG. 2. The angular velocity sensor 4, the acceleration sensor 5 and the circuit unit 6 are fixed to the chassis 3.

The angular velocity sensor 4 is a sensor that detects a spatial (three-dimensional space) angular velocity vector. The angular velocity sensor 4 is constituted of a three-axis angular velocity sensor that generates detection outputs of angular velocities in three detection axis directions (the components in the detection axis directions of an angular velocity vector).

The acceleration sensor 5 is a sensor that detects a spatial (three-dimensional space) translational acceleration vector. The acceleration sensor 5 is constituted of a three-axis acceleration sensor that generates detection outputs of accelerations in three detection axis directions (the components in the detection axis directions of a translational acceleration vector).

The three-axis angular velocity sensor 4 may use a combination of three separate single-axis angle sensors having detection axis directions that are different from each other or three single-axis angle sensors that are integrated. The same applies to the three-axis acceleration sensor 5.

In the present embodiment, the three detection axis directions of the angular velocity sensor 4 of each of the sensor units 2 are orthogonal to each other and the three detection axis directions of the acceleration sensor 5 thereof are also orthogonal to each other. Further, the angular velocity sensor 4 and the acceleration sensor 5 are mounted on the sensor unit 2 such that the three detection axis directions of the angular velocity sensor 4 and the three detection axis directions of the acceleration sensor 5 are the same directions.

For example, as illustrated in FIG. 2, the axis directions (x-axis direction, y-axis direction and z-axis direction) of an xyz orthogonal coordinate system Cs fixedly set to the sensor unit 2 (hereinafter referred to as the sensor unit local coordinate system Cs) are the detection axis directions common to the angular velocity sensor 4 and the acceleration sensor 5.

Alternatively, however, the three detection axis directions of the angular velocity sensor 4 and the three detection axis directions of the acceleration sensor 5 of each of the sensor units 2 may be different from each other. Further alternatively, the three detection axis directions of the angular velocity sensor 4 or the three detection axis directions of the acceleration sensor 5 may not be orthogonal to each other except for the case where two or more detection axis directions are parallel to each other.

In this case, the mutual layout relationship between the angular velocity sensor 4 and the acceleration sensor 5 is maintained constant. Hence, a detection value of the same detection axis direction can be obtained for the angular velocity sensor 4 and the acceleration sensor 5 from the detection value of an angular velocity vector detected by the angular velocity sensor 4 or the detection value of an acceleration vector detected by the acceleration sensor 5 by coordinate transformation.

Figure 3:
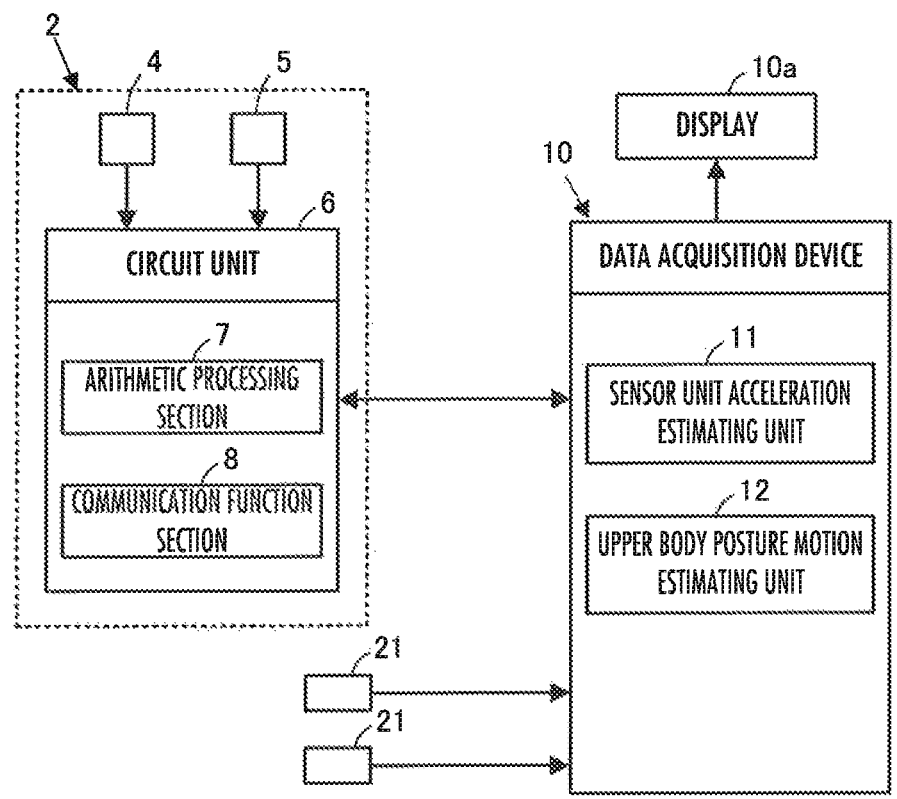
FIG. 3 is a block diagram illustrating the configuration related to the operation of the upper body motion measurement system of the embodiment.

The circuit unit 6 of each of the sensor units 2 includes an arithmetic processing section 7 and a communication function section 8, as illustrated in FIG. 3.

The arithmetic processing section 7 is a circuit section that includes a CPU, a memory and the like. The arithmetic processing section 7 functions as a sensor unit attitude estimating unit that estimates the spatial attitude (spatial orientation) of the sensor unit 2 on which the circuit unit 6 including the arithmetic processing section 7 is mounted, the functions thereof being implemented by running an installed program or implemented by a hardware configuration.

The arithmetic processing section 7 having the foregoing functions acquires the detection outputs of the angular velocity sensor 4 and the acceleration sensor 5 through the intermediary of an input circuit (not illustrated) of an amplifier, an A/D converter or the like. Then, the arithmetic processing section 7 carries out predetermined arithmetic processing, such as publicly known strap-down calculation, by using the detection value of the angular velocity vector indicated by a detection output of the angular velocity sensor 4 and the detection value of the acceleration vector indicated by a detection output of the acceleration sensor 5, thereby estimating the spatial attitude of the sensor unit 2 in the motion environment of the subject P.

The attitude of the sensor unit 2 estimated by the arithmetic processing section 7 is expressed as an attitude observed in a global coordinate system Cg set in the travel environment of the subject P, as illustrated in FIG. 1A and FIG. 1B. The global coordinate system Cg uses, for example, an XYZ orthogonal coordinate system having the direction of an axis, which is obtained by projecting the x-axis of the sensor unit local coordinate system Cs onto a horizontal plane, as an X-axis direction thereof, the vertical direction (a gravity direction) as a Z-axis direction thereof, and a direction that is orthogonal to the X-axis and the Z-axis as a Y-axis direction.

The communication function section 8 is composed of communication equipment for wireless communication or wired communication and a communication circuit accompanying the communication equipment. The communication function section 8 transmits the measurement data indicating the attitude of the sensor unit 2 estimated by the arithmetic processing section 7 and the measurement data indicating the detection value of the acceleration (the translational acceleration vector) of the sensor unit 2 indicated by a detection output of the acceleration sensor 5 to the data acquisition device 10 wirelessly or wiredly.

According to the present embodiment, the two sensor units 2 configured as described above are attached to the back (dorsal surface) of the upper body of the subject P with a vertical interval provided therebetween, as illustrated in FIG. 1A and FIG. 1B.

Specifically, according to the present embodiment, one of the two sensor units 2, 2 is attached to a place on the upper side from the boundary between the twelfth thoracic vertebra (the bottom vertebra in the thoracic vertebra) and the first lumbar vertebra (the top vertebra in the lumbar vertebra) on a line along the spine of the back of the upper body of the subject P (along the trunk axis L), the boundary being hereinafter referred to as the thoracic vertebra/lumbar vertebra boundary. The other of the two sensor units 2, 2 is attached to a place on the lower side from the thoracic vertebra/lumbar vertebra boundary (a place in the vicinity of the waist).

More specifically, the sensor unit 2 on the upper side is attached to, for example, a place in the vicinity of the base of the neck of the subject P (a place in the vicinity of the top vertebra in the thoracic vertebra (the first thoracic vertebra)). Further, the sensor unit 2 on the lower side is attached to, for example, a place in the vicinity of the bottom vertebra of the lumbar vertebra (the fifth lumbar vertebra).

Here, in the upper body of a person, the part where the lumbar vertebra is located corresponds to a main bending part (the part of the center of rotation) of the upper body when the posture of the upper body is changed in the pitch direction or the roll direction. Hence, the sensor unit 2 on the lower side is attached to the upper body at the place in the vicinity of the center of rotation in a change of the posture of the upper body.

Further, the ribs come in contact with the thoracic vertebra, so that the part where the thoracic vertebra is located is more rigid than the part where the lumbar vertebra or the like is located. Accordingly, the sensor unit 2 on the upper side is attached to the upper body at a place adjacent to the upper end of the part that is highly rigid in the upper body.

Supplementarily, the sensitivity to a change in the difference between the accelerations (the accelerations in the X-axis direction or the Y-axis direction) of the sensor units 2, 2 in response to a change in the angular velocity of the upper body becomes higher in the case where the distance between the sensor units 2, 2 in the vertical direction is larger than in the case where the distance therebetween is smaller. Hence, when estimating (measuring) the angular acceleration (the angular acceleration in the pitch direction or the angular acceleration in the roll direction) of the upper body of the subject P as will be discussed hereinafter, the resolution of the estimation of the angular velocity of the upper body can be made higher in the case where the distance between the sensor units 2, 2 in the vertical direction is larger than in the case where the distance therebetween is smaller.

The places where the sensor units 2, 2 are attached are not limited to the foregoing example. For instance, at least one of the sensor units 2, 2 may be attached to the front side (the chest or the belly) of the subject P. Further, the sensor units 2, 2 may be attached to the subject P at positions of different heights from those of the foregoing example.

The sensor units 2 are attached to the back of the upper body of the subject P through an appropriate attaching member. For instance, the subject P wears a leotard or other garment that is stretchy and keeps very close contact with the upper body of the subject P. The chassis 3 of each of the sensor units 2 is fixed to the garment on the upper body of the subject P through an attaching member, such as a Velcro tape. Thus, the sensor units 2 are attached to the upper body so as to be capable of performing a translational motion together or substantially together with the parts of the upper body to which the sensor units 2 are attached.

In this case, each of the sensor units 2 is attached to the upper body of the subject P such that the x-axis direction of the sensor unit local coordinate system Cs illustrated in FIG. 2 coincides or substantially coincides with the normal direction of the contact surface of the sensor unit 2 relative to the upper body of the subject P (i.e. the longitudinal direction of the upper body of the subject P), the y-axis direction thereof coincides or substantially coincides with the lateral direction (the width direction) of the upper body of the subject P, and the z-axis direction thereof coincides or substantially coincides with the vertical direction (the direction of the trunk axis L) of the upper body of the subject P.

The form in which the sensor units 2 are attached to the subject P is not limited to the foregoing form. For example, the sensor units 2 may be mounted on a belt that is attached to the upper body of the subject P. Alternatively, the sensor units 2 may be directly attached to the skin of the upper body of the subject P by tape or the like.

The data acquisition device 10 is composed of, for example, a computer having a display 10a. The data acquisition device 10 receives a signal indicating an estimated value of the attitude of each of the sensor units 2 by the communication with the circuit unit 6 of each of the sensor units 2.

The data acquisition device 10 may alternatively be composed of a plurality of computers or electronic circuit units, which permit mutual communication. Further, the data acquisition device 10 may include a printing machine or the like.

Further, the data acquisition device 10 includes, as a function implemented by an installed program or a function implemented by a hardware configuration, a sensor unit acceleration estimating unit 11 that estimates the acceleration of each of the inertia sensor units 2 observed in the global coordinate system Cg and an upper body posture motion estimating unit 12 that estimates a change in the posture of the upper body, including the angular acceleration of the upper body of the subject P observed in the global coordinate system, as illustrated in FIG. 3.

The sensor unit acceleration estimating unit 11 has the function as the sensor unit acceleration estimating unit in the present invention. Further, the upper body posture motion estimating unit 12 has a function as the upper body angular acceleration estimating unit and the upper body angular velocity estimating unit in the present invention.

The upper body motion measurement system 1 according to the present embodiment further includes ground contact sensors 21, 21 for detecting the landing/leaving of each leg of the subject P on/from a floor, as illustrated in FIG. 1A. Each of the ground contact sensors 21 is composed of a pressure-sensitive switch and the like. The ground contact sensors 21 are attached to, for example, the soles of shoes worn on the feet of the subject P. Further, the ground contact sensor 21 of each leg outputs an ON signal when the foot of the leg lands on the floor, and outputs an OFF signal when the foot of the leg leaves from the floor. In this case, the output signal of the ground contact sensor 21 of each leg is transmitted wirelessly or wiredly to the data acquisition device 10 through a communication device, which is not illustrated.

A description will now be given of the details of the processing carried out by each function section of the data acquisition device 10 and the processing for measuring a change in the posture of the upper body of the subject P by the upper body motion measurement system 1 according to the present embodiment.

First, the sensor units 2, 2 and the data acquisition device 10 are started. Further, the two sensor units 2, 2 are attached to the upper body of the subject P as described above, and the subject P puts the shoes provided with the ground contact sensors 21 on to his/her feet. At this time, the processing for initial setting, such as the setting for synchronizing the time on a timer or mutual recognition of the time on the timer, is carried out between the sensor units 2, 2 and the data acquisition device 10.

In this state, the subject P starts walking (straight walking) The walking is carried out with a number of steps, namely, 2*n steps (n denoting a predetermined integer value of two or more, and "*" denoting a multiplication sign). The subject P may put on an appropriate walking aid.

During the walking, the arithmetic processing section 7 of each of the sensor units 2, which has the function as the sensor unit attitude estimating unit, sequentially acquires the detection outputs of the angular velocity sensor 4 and the acceleration sensor 5 to sequentially estimate the spatial attitude of each of the sensor units 2 by a technique, such as the strap-down calculation. The estimated value of the attitude of each of the sensor units 2 is represented by, for example, an Euler angle. However, the attitude of each of the sensor units 2 may be also represented in the form of a quarternion or an attitude matrix.

Specifically, the arithmetic processing section 7 carries out calculation for integrating the detection values of the angular velocity (the angular velocity vector constituted of three-axis components) indicated by the detection outputs of the angular velocity sensor 4 thereby to sequentially calculate the basic value of an instantaneous attitude of each of the sensor units 2.

Further, the arithmetic processing section 7 sequentially calculates the instantaneous attitude (the tilt angles in the pitch direction and the roll direction) of each of the sensor units 2 with respect to the gravity direction (the vertical direction) based on the detection value of the acceleration (a translational acceleration vector constituted of three-axis components) indicated by the detection output of the acceleration sensor 5.

Further, the arithmetic processing section 7 calculates the difference between the basic value of the instantaneous attitude based on the detection output of the angular velocity sensor 4 and the instantaneous attitude based on the detection output of the acceleration sensor 5.

Here, the acceleration detected by the acceleration sensor 5 includes a gravitational acceleration vector. Further, the magnitude of the horizontal direction component of the translational acceleration vector detected by the acceleration sensor 5 is usually sufficiently smaller than the magnitude of the gravitational acceleration vector. Therefore, the long-term average value of the translational acceleration vectors detected by the acceleration sensor 5 substantially coincides with the gravitational acceleration vector.

Thus, the arithmetic processing section 7 corrects the basic value of the instantaneous attitude based on the detection output of the angular velocity sensor 4 according to the foregoing difference so as to converge the difference to zero in the long term, thereby calculating the estimated value of the attitude of each of the sensor units 2.

As the technique for estimating the attitude of each of the sensor units 2, a publicly known technique, such as the strap-down calculation, may be adopted as described above.

The measurement data indicating the attitude of each of the sensor units 2 sequentially estimated by the arithmetic processing section 7 of the sensor unit 2 is transmitted to the data acquisition device 10 by the communication function section 8 of the sensor unit 2. Further, the measurement data indicating the detection values of the translational acceleration vector indicated by the detection outputs of the acceleration sensor 5 of the sensor unit 2 is also transmitted to the data acquisition device 10 by the communication function section 8.

The processing for estimating the attitude of each of the sensor units 2 can be carried out also by the data acquisition device 10. This means that the data acquisition device 10 may be provided with a function as the sensor unit attitude estimating unit. In this case, the measurement data indicating the detection outputs of the angular velocity sensor 4 and the acceleration sensor 5 of the sensor unit 2 is transmitted to the data acquisition device 10 from the sensor unit 2.

Supplementarily, other than the angular velocity sensor 4 and the acceleration sensor 5, a sensor, such as a camera, mounted on the sensor unit 2 may be used to estimate the acceleration (the translational acceleration) in the horizontal direction of the sensor unit 2 (a direction substantially parallel to a floor surface). In this case, the gravitational acceleration vector observed in the sensor unit local coordinate system Cs can be determined by subtracting the estimated value of the acceleration vector in the horizontal direction from the acceleration vector detected by the acceleration sensor 5. Consequently, based on the gravitational acceleration vector, the instantaneous attitude of the sensor unit 2 relative to the gravity direction can be estimated.

Further, if each of the sensor units 2 is provided with a geomagnetic sensor, then it is possible to make a drift correction of a yaw-direction component in the angular velocity indicated by a detection output of the angular velocity sensor 4.

The measurement data transmitted from each of the sensor units 2 to the data acquisition device 10 (specifically, the measurement data indicating the estimated value and the detection value of the translational acceleration vector of the attitude of the sensor unit 2 at each time while the subject P is walking) is stored and retained in a storage medium, such as a memory, of the data acquisition device 10 in a time series manner.

Then, the data acquisition device 10 carries out the processing for analyzing or assessing the motion of the upper body of the subject P by using the measurement data according to the flowchart of FIG. 4 (the processing including the processing by the sensor unit acceleration estimating unit 11 and the upper body posture motion estimating unit 12).

In the following description, to distinguish the two sensor units 2, 2, one of the sensor units 2 (e.g. the sensor unit 2 on the upper side) will be referred to as the first sensor unit 2 and the other sensor unit 2 (e.g. the sensor unit 2 on the lower side) as the second sensor unit 2 in some cases. Further, an arbitrary one of the first sensor unit 2 and the second sensor unit 2 may be referred to as an i-th sensor unit 2 (i=1 or 2) in some cases.

Further, the sensor unit local coordinate system Cs corresponding to the i-th sensor unit 2 will be referred to as an i-th local coordinate system Cs_i. Further, the global coordinate system Cg having, as the X-axis direction thereof, the direction of an axis obtained by projecting the x-axis of the i-th local coordinate system Cs_i onto a horizontal plane will be referred to as the i-th global coordinate system Cg_i.

Supplementarily, all of the X-axis direction, the Y-axis direction and the Z-axis direction of the i-th global coordinate system Cg_i corresponding to each of the sensor units 2 are the same or substantially the same direction to each other on either of the sensor units 2. For this reason, the i-th global coordinate system Cg_i will, in some cases, be referred to simply as the global coordinate system Cg without distinguishing the i-th global coordinate systems Cg_i from each other.

In the description of the present embodiment, the positive directions of the X-axis, the Y-axis and the Z-axis of the global coordinate system Cg are defined as the frontward direction, the leftward direction and the upward direction, respectively, as observed from the subject P. The positive directions of the x-axis, the y-axis and the z-axis of the sensor unit local coordinate system Cs (the i-th local coordinate system Cs_i) are defined as the frontward direction, the leftward direction and the upward direction, respectively, of the upper body of the subject P.

Referring to FIG. 4, the data acquisition device 10 first acquires in STEP1 the measurement data of the gait for 2*n steps from the measurement data stored and retained in the storage medium. Here, the measurement data of the gait for one step (hereinafter referred to as the element gait) is the measurement data of the period from the switching timing at which the supporting leg (or the free leg) of the subject P is switched from one leg to the other leg to the next switching timing.

For example, according to the present embodiment, the period from the timing at which the landing (or leaving) of one of the legs of the subject P on (or from) a floor is detected by the ground contact sensor 21 of the one leg to the timing at which the landing (or leaving) of the other leg is detected by the ground contact sensor 21 of the other leg is defined as the period of the element gait. Then, the data acquisition device 10 acquires the measurement data of the period of consecutive 2*n element gaits (hereinafter referred to as the 2n gait) as the measurement data of the gait for 2*n steps.

The element gait of the first step of the 2n gait may be the element gait of any number of step after the subject P actually starts walking. For example, the gait of the number of step (e.g. the third step in the actual walking) which is considered to indicate that the walking state of the subject P has reached a normal walking state may be acquired as the measurement data indicative of the first-step element gait of the 2n gait.

Subsequently, in STEP2, the data acquisition device 10 calculates, for each of the sensor units 2, an i-th global acceleration vector, which is an acceleration vector (instantaneous value) of the i-th sensor unit 2 observed in the i-th global coordinate system Cg_i at each time t during the period of the 2n gait (sampling time for each predetermined arithmetic processing cycle from the start time of the 2n gait).

Hereinafter, $\uparrow$acc_i_global or $\uparrow$acc_i_global(t) will be used as the reference character denoting the i-th global acceleration vector. Further, the acceleration vector (instantaneous value) of the i-th sensor unit 2 observed in the i-th local coordinate system Cs_i will be referred to as the i-th local acceleration vector, and $\uparrow$acc_i_local or $\uparrow$acc_i_local(t) will be used as the reference character thereof.

The symbol "$\uparrow$" in the reference character denotes a vector formed of a plurality of components, and the (t) at the end denotes a value at time t.

The i-th global acceleration vector $\uparrow$acc_i_global(t) is calculated according to expression (1) given below from the detection value of the i-th local acceleration vector $\uparrow$acc_i_local(t) indicated by the detection output of the acceleration sensor 5 of the i-th sensor unit 2 at time t and a rotation matrix (attitude transformation matrix) M_i(t) defined by the estimated value of the attitude (the attitude observed in the i-th global coordinate system Cg_i) of the i-th sensor unit 2 at time t.

$$\uparrow acc\_i\_global(t) = M\_i(t) * \uparrow acc\_i\_local(t) \quad (1)$$

where $$\uparrow acc\_i\_global(t) \equiv [acc\_i\_x\_global(t), acc\_i\_y\_global(t), acc\_i\_z\_global(t)]^T$$

acc_i_x_global(t): X-axis direction component of $\uparrow$acc_i_global(t)

acc_i_y_global(t): Y-axis direction component of $\uparrow$acc_i_global(t)

acc_i_z_global(t): Z-axis direction component of $\uparrow$acc_i_global(t)     (1a)

$$\uparrow acc\_i\_local(t) \equiv [acc\_i\_x\_local(t), acc\_i\_y\_local(t), acc\_i\_z\_local(t)]^T$$

acc_i_x_local(t): x-axis direction component of $\uparrow$acc_i_local(t)

acc_i_y_local(t): y-axis direction component of $\uparrow$acc_i_local(t)

acc_i_z_local(t): z-axis direction component of $\uparrow$acc_i_local(t)     (1b)

$$M\_i(t) \equiv \begin{pmatrix} \cos\theta y(t) & \sin\theta x(t) * \sin\theta y(t) & \cos\theta x(t) * \sin\theta y(t) \\ 0 & \cos\theta x(t) & -\sin\theta x(t) \\ -\sin\theta y(t) & \sin\theta x(t) * \cos\theta y(t) & \cos\theta x(t) * \cos\theta y(t) \end{pmatrix} \quad (1c)$$

θx(t): Euler angle in the direction about X-axis at time t

θy(t): Euler angle in the direction about Y-axis at time t

The superscript "T" of the right sides of expressions (1a) and (1b) given above means transposition. Further, the first sequence, the second sequence and the third sequence of the rotation matrix M_i(t) represented by expression (1c) mean the basis vector of the x-axis, the basis vector of the y-axis, and the basis vector of the z-axis, respectively, of the i-th local coordinate system observed in the i-th global coordinate system.

In the present embodiment, the Z-axis direction component acc_i_z_global(t) of the i-th global acceleration vector $\uparrow$acc_i_global will not be used in the processing hereinafter. Hence, the processing for calculating the Z-axis direction component acc_i_z_global(t) may be omitted.

Next, in STEP3, the data acquisition device 10 calculates an average value ave_period_R of an R support gait period, period_R_k (k=1, 2, . . . , n), which denotes the time width of each period of an n number of element gaits in which the right leg of the subject P becomes the supporting leg (hereinafter referred to as the R support gait) in the 2n gait (the time width extending from the start to the end of each R support gait), and an average value ave_period_L of an L support gait period, period_L_k (k=1, 2, . . . , n), which denotes the time width of each period of the n number of element gaits in which the left leg of the subject P becomes the supporting leg (hereinafter referred to as the L support gait) according to expressions (2a) and (2b), respectively, given below.

$$ave\_period\_R = (period\_R\_1 + period\_R\_2 + \ldots + period\_R\_n)/n \quad (2a)$$

$$ave\_period\_L = (period\_L\_1 + period\_L\_2 + \ldots + period\_L\_n)/n \quad (2b)$$

Subsequently, in STEP4, the data acquisition device 10 calculates a normalization R support gait period norm_period_R and a normalization L support gait period norm_period_L to normalize the time axis of each of the R support gait and the L support gait.

The normalization R support gait period norm_period_R and the normalization L support gait period norm_period_L are determined such that the total sum thereof (=norm_period_R+norm_period_L) will be an arbitrary constant value (≠0) and that the ratio between norm_period_R and norm_period_L coincides with the ratio between ave_period_R and ave_period_L.

Specifically, the data acquisition device 10 calculates norm_period_R and norm_period_L according to expressions (3a) and (3b) given below.

$$\text{norm\_period\_}R = T\text{norm}^* \text{ave\_period\_}R/(\text{ave\_period\_}R + \text{ave\_period\_}L) \quad (3a)$$

$$\text{norm\_period\_}L = T\text{norm}^* \text{ave\_period\_}L/(\text{ave\_period\_}R + \text{ave\_period\_}L) \quad (3b)$$

Tnorm (=norm_period_R+norm_period_L) in expressions (3a) and (3b) denotes a constant value Tnorm (≠0) arbitrarily set as a value denoting a normalized time width of the period of the two-step gait, and is set to, for example, 1. Hereinafter, Tnorm will be referred to as the normalization reference time width.

The normalization reference time width Tnorm may take a constant value other than 1 and may be, for example, Tnorm=ave_period_R+ave_period_L. In such a case, norm_period_R=ave_period_R and norm_period_L=ave_period_L, thus substantially obviating the need for the processing in STEP4.

Subsequently, in STEP5, the data acquisition device 10 normalizes the time axis, which represents the waveform of each component of the i-th global acceleration vector ↑acc_i_global in the period of each of the R support gait and the L support gait constituting the 2n gait, to a time axis having the normalization reference time width Tnorm as the time width of the period of the two-step gait.

The normalization processing is accomplished by scale-converting (enlarging or reducing) the waveform of each component of the i-th global acceleration vector ↑acc_i_global in the time axis direction for each element gait of the 2n gait such that each R support gait period and each L support gait period of the 2n gait coincide with norm_period_R and norm_period_L, respectively.

In this case, if the actual time width of the R support gait period is denoted by T_R, then the enlargement or reduction rate in the time axis direction of the waveform of each component of the i-th global acceleration vector ↑acc_i_global in each R support gait will be (norm_period_R/T_R). Similarly, if the actual time width of the L support gait period is denoted by T_L, then the enlargement or reduction rate in the time axis direction of the waveform of each component of the i-th global acceleration vector ↑acc_i_global in each L support gait will be denoted by (norm_period_L/T_L).

By the processing in STEP5 described above, the waveforms of the components of the i-th global acceleration vector ↑acc_i_global in each R support gait of the 2n gait are scale-converted in the time axis direction into waveforms having the same time width (=norm_period_R). Similarly, the waveforms of the components of the i-th global acceleration vector ↑acc_i_global in each L support gait of the 2n gait are scale-converted in the time axis direction into waveforms having the same time width (=norm_period_L).

Hereinafter, the i-th global acceleration vector ↑acc_i_global with the time axis thereof normalized as described above will be denoted by the normalized i-th global acceleration vector ↑norm_acc_i_global, and the X-axis direction component, the Y-axis direction component and the Z-axis direction component thereof will be denoted by norm_acc_i_x_global, norm_acc_i_y_global and norm_acc_i_z_global, respectively. Further, the time axis that has been normalized will be referred to as the normalized time axis.

Figure 5A:
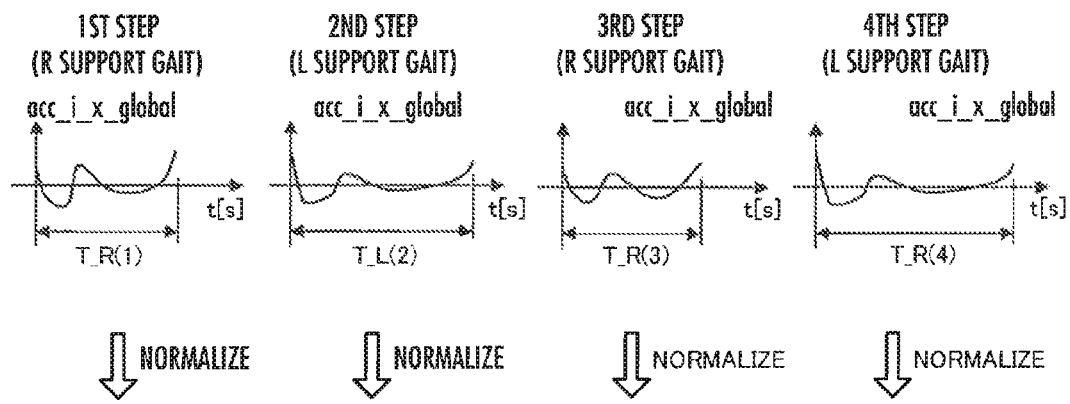
FIG. 5A, FIG. 5B and FIG. 5C are explanatory diagrams related to the processing in STEP 5 and STEP6 in FIG. 4.
Figure 5B:
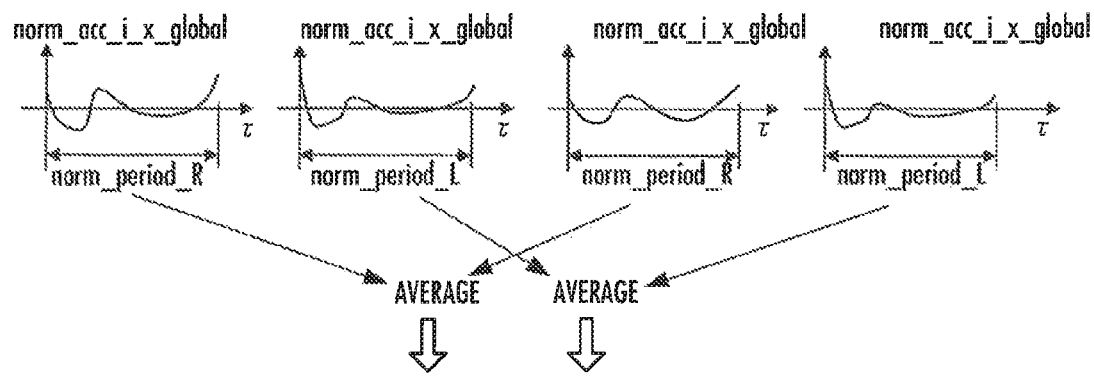

FIG. 5A and FIG. 5B respectively illustrate an example of the waveform (the waveform on an actual time axis) of one of the components of the i-th global acceleration vector ↑acc_i_global, e.g. the X-axis direction component acc_i_x_global, and an example of the waveform (the waveform on the normalized time axis) of the X-axis direction component norm_acc_i_x_global of the normalized i-th global acceleration vector ↑norm_acc_i_global obtained by the foregoing normalization processing. FIG. 5A illustrates the waveforms of acc_i_x_global in each element gait of the first step, the second step, the third step and the fourth step of the 2n gait. FIG. 5B illustrates the waveforms of norm_acc_i_x_global in each element gait of the first step, the second step, the third step and the fourth step.

In the illustrated examples, the element gaits of the odd-numbered steps (the first step and the third step) are the R support gaits, while the element gaits of the even-numbered steps (the second step and the fourth step) are the L support gaits. Further, the axis of abscissas denoted by a reference character t indicates the time axis in FIG. 5A, and the axis of abscissas denoted by a reference character τ indicates the normalized time axis in FIG. 5B.

As illustrated, in both the R support gaits and the L support gaits, the waveforms of the normalized i-th global acceleration vector ↑norm_acc_i_global will be the waveforms having the same time width on the normalized time axis.

Subsequently, in STEP6, the data acquisition device 10 generates average waveform data obtained by averaging the waveforms of the components of the normalized i-th global acceleration vector ↑norm_acc_i_global of an n number of R support gaits of the 2n gait and the waveforms of the components of the normalized i-th global acceleration vector ↑norm_acc_i_global of an n number of L support gaits.

Specifically, the average value for each component of the normalized i-th global acceleration vector ↑norm_acc_i_global(τ) of each of the n number of R support gaits at each time τ on the normalized time axis related to the R support gaits (each time for each predetermined interval from the start time of each R support gait on the normalized time axis) is calculated so as to generate the average waveform data of each component of the normalized i-th global acceleration vector ↑norm_acc_i_global of the n number of R support gaits.

Similarly, the average value for each component of the normalized i-th global acceleration vector ↑norm_acc_i_global(τ) of each of the n number of L support gaits at each time τ on the normalized time axis related to the L support gaits (the time for each predetermined interval from the start time of each L support gait on the normalized time axis) is calculated so as to generate the average waveform data of each component of the normalized i-th global acceleration vector ↑norm_acc_i_global of the n number of L support gaits.

The suffix (τ) of the reference character denotes the value at time τ on the normalized time axis.

Hereinafter, the value (instantaneous value) of the normalized i-th global acceleration vector ↑norm_acc_i_global in the foregoing average waveform data related to the R support gait will be referred to as the R-side normalized i-th average acceleration vector, and the value (instantaneous value) of the normalized i-th global acceleration vector ↑norm_acc_i_global in the foregoing average waveform data related to the L support gait will be referred to as the L-side normalized i-th average acceleration vector. Further, ↑norm_R_ave_acc_i_global will be used as the reference character of the R-side normalized i-th average acceleration vector, and ↑norm_L_ave_acc_i_global will be used as the reference character of the L-side normalized i-th average acceleration vector.

Further, the R-side normalized i-th average acceleration vector and the L-side normalized i-th average acceleration vector will be generically referred to as the normalized i-th average acceleration vectors, and ↑norm_ave_acc_i_global will be used as the reference character thereof.

Figure 5C:
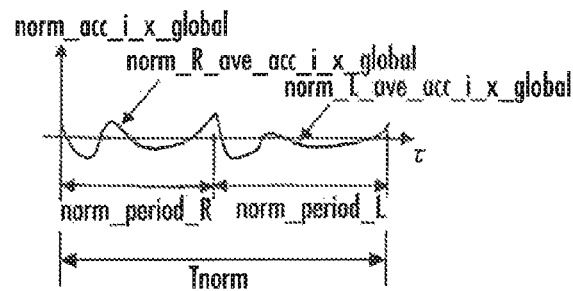

FIG. 5C illustrates the example of the waveform indicated by the average waveform data of the R support gait obtained by the processing in STEP6 described above (e.g. the waveform of the X-axis direction component norm_R_ave_acc_i_x_global of ↑norm_R_ave_acc_i_global) and the example of the waveform indicated by the average waveform data of the L support gait (e.g. the waveform of the X-axis direction component norm_L_ave_acc_i_x_global of ↑norm_L_ave_acc_i_global), which are arranged side by side on the normalized time axis.

According to the present embodiment, the waveform in which the waveform of the R-side normalized i-th average acceleration vector ↑norm_R_ave_acc_i_global and the waveform of the L-side normalized i-th average acceleration vector ↑norm_L_ave_acc_i_global are arranged side by side as illustrated in FIG. 5C on the normalized time axis for each component (hereinafter referred to as the RL normalized i-th average acceleration vector waveform) is used as the waveform of the average waveform data of the i-th acceleration vector ↑acc_i_global in the period of the two-step gait of the subject P (the period of the time width of Tnorm on the normalized time axis).

The order of arrangement of the waveform of the R-side normalized i-th average acceleration vector ↑norm_R_ave_acc_i_global and the waveform of the L-side normalized i-th average acceleration vector ↑norm_L_ave_acc_i_global in the RL normalized i-th average acceleration vector waveform may be either the R-side and the L-side or the L-side and the R-side.

The waveform of the R-side normalized i-th average acceleration vector ↑norm_R_ave_acc_i_global corresponds to the waveform obtained by representing the waveform of the average i-th acceleration vector ↑acc_i_global in the R support gait of the subject P on the normalized time axis. Further, the waveform of the L-side normalized i-th average acceleration vector ↑norm_L_ave_acc_i_global corresponds to the waveform obtained by representing the waveform of the average i-th acceleration vector ↑acc_i_global in the L support gait of the subject P on the normalized time axis.

In the following description, the R support gait corresponding to the waveform of the R-side normalized i-th average acceleration vector ↑norm_R_ave_acc_i_global will be referred to as the normalized average R support gait, and the L support gait corresponding to the waveform of the L-side normalized i-th average acceleration vector ↑norm_L_ave_acc_i_global will be referred to as the normalized average L support gait. Further, the two-step gait consisting of the normalized average R support gait and the normalized average L support gait, which are consecutive (the gait corresponding to the RL normalized i-th average acceleration vector waveform) will be referred to as the two-step normalized average gait.

Supplementarily, according to the present embodiment, the processing in STEP2 to STEP6 described above is carried out by the sensor unit acceleration estimating unit 11 corresponding to the sensor unit acceleration estimating unit in the present invention. In this case, each component of the i-th global acceleration vector ↑acc_i_global of each of the sensor units 2 corresponds to the target state amount in the present invention. Further, the processing in STEP2 corresponds to the basic estimated value generation processing in the present invention, and the processing in STEP3 to STEP6 corresponds to the average waveform data generation processing.

Next, in STEP7, the data acquisition device 10 calculates the angular acceleration of the upper body of the subject P (the instantaneous value at each time τ in the period of the two-step normalized average gait) by using the data of the foregoing RL normalized i-th average acceleration vector waveform (the average waveform data). In the present embodiment, the angular acceleration calculated in this STEP7 includes an angular acceleration θx_dot2_with_offset in the roll direction (the direction about the X-axis) of the upper body of the subject P, and an angular acceleration θy_dot2_with_offset in the pitch direction (the direction about the Y-axis) of the upper body of the subject P. The angular accelerations θx_dot2_with_offset and θy_dot2_with_offset are the angular accelerations before the offset components, which will be discussed hereinafter, are eliminated.

Here, the sensor units 2 are sufficiently small compared with the upper body of the subject P, and the areas of the surfaces (contact surfaces) of the upper body of the subject P to which the sensor units 2 are attached are relatively small. Hence, the instantaneous attitude of each of the sensor units 2 tends to deviate from the actual instantaneous posture of the upper body of the subject P. This tends to cause the instantaneous value of the angular acceleration of each of the sensor units 2 to deviate from the instantaneous value of an actual angular acceleration of the upper body of the subject P.

Meanwhile, the translational accelerations of the sensor units 2 relatively closely follow the translational accelerations of the places of the upper body of the subject P where the sensor units 2 are attached. Therefore, a change in the difference in the Y-axis direction translational acceleration of each of the sensor units 2, 2 relatively closely follows a change in the angular acceleration in the roll direction (the direction about the X-axis) of the upper body of the subject P. Similarly, a change in the difference in the X-axis direction translational acceleration of each of the sensor units 2, 2 relatively closely follows a change in the angular acceleration in the pitch direction (the direction about the Y-axis) of the upper body of the subject P.

Accordingly, in STEP7, the data acquisition device 10 calculates the angular acceleration θx_dot2_with_offset in the roll direction (the X-axis direction) of the upper body of the subject P by the linear combination indicated in expression (4a) below from the Y-axis direction component norm_ave_acc_1_y_global of a normalized first average acceleration vector ↑norm_ave_acc_1_global of the first sensor unit 2 (the upper sensor unit 2) of the sensor units 2 and the Y-axis direction component norm_ave_acc_2_y_global of a normalized second average acceleration vector ↑norm_ave_acc_2_global of the second sensor unit 2 (the lower sensor unit 2).

Further, the data acquisition device 10 calculates the angular acceleration θy_dot2_with_offset in the pitch direction (the Y-axis direction) of the upper body of the subject P by the linear combination indicated in expression (4b) below from the X-axis direction component norm_ave_acc_1_x_global of the normalized first average acceleration vector ↑norm_ave_acc_1_global of the first sensor unit 2 and the X-axis direction component norm_ave_acc_2_x_global of the normalized second average acceleration vector ↑norm_ave_acc_2_global of the second sensor unit 2.

$$\theta x\_dot2\_with\_offset(\tau)=-(norm\_ave\_acc\_1\_y\_global(\tau)-norm\_ave\_acc\_2\_y\_global(\tau))/(h1-h2) \quad (4a)$$

$$\theta y\_dot2\_with\_offset(\tau)=(norm\_ave\_acc\_1\_x\_global(\tau)-norm\_ave\_acc\_2\_x\_global(\tau))/(h1-h2) \quad (4b)$$

where
h1: Height of the first sensor unit 2 from a floor surface
h2: Height of the second sensor unit 2 from a floor surface (<h1)

"h1−h2" that defines the coefficient of each item of the right sides in expressions (4a) and (4b) given above corresponds to the distance in the vertical direction between the first sensor unit 2 and the second sensor unit 2.

As the values of h1 and h2, the values of the heights of the first sensor unit 2 and the second sensor unit 2 when the subject P is standing upright, which are measured in advance (fixed values), are used.

The value of the angular acceleration calculated in STEP7 as described above usually includes an offset component due to a drift or the like of a detection output of the angular velocity sensor 4 or the acceleration sensor 5 of each of the sensor units 2.

Hence, the data acquisition device 10 then carries out the processing for removing the offset component in STEP8.

Here, in general, the average value of the actual angular accelerations of the upper body in the period of the two-step gait of normal straight-ahead walking of a person becomes zero or substantially zero. Therefore, an average value θx_dot2_ave of the angular acceleration in the roll direction in the two-step normalized average gait θx_dot2_with_offset(τ) and an average value θy_dot2_ave of the angular acceleration in the pitch direction θy_dot2_with_offset(τ) can be regarded to correspond to the offset component of θx_dot2_with_offset(τ) and the offset component of θy_dot2_with_offset(τ), respectively.

Hence, in STEP8, the data acquisition device 10 calculates the average value θx_dot2_ave of the angular acceleration in the roll direction θx_dot2_with_offset of the upper body of the subject P in the two-step normalized average gait and the average value θy_dot2_ave of the angular acceleration in the pitch direction θy_dot2_with_offset thereof according to expressions (5a) and (5b) given below.

$$\theta x\_dot2\_ave=(1/Tnorm)*\int_0^{Tnorm}(\theta x\_dot2\_with\_offset(\tau))d\tau \quad (5a)$$

$$\theta y\_dot2\_ave=(1/Tnorm)*\int_0^{Tnorm}(\theta y\_dot2\_with\_offset(\tau))d\tau \quad (5b)$$

Then, the data acquisition device 10 calculates the value obtained by subtracting the average value θx_dot2_ave (offset component), which has been calculated as described above, from the angular acceleration θx_dot2_with_offset(τ) in the roll direction at each time T in the two-step normalized average gait, and the value obtained by subtracting the average value θy_dot2_ave (offset component), which has been calculated as described above, from the angular acceleration θy_dot2_with_offset(τ) in the pitch direction as the estimated value of an actual angular acceleration θx_dot2(τ) in the roll direction (the estimated value after removing the offset component) of the upper body of the subject P in the two-step normalized average gait and the estimated value of the angular acceleration θy_dot2(τ) in the pitch direction (the estimated value after removing the offset component), respectively, as indicated by expressions (6a) and (6b) given below. Thus, the waveform data of the estimated values of the angular accelerations θx_dot2(τ) and θy_dot2(τ) of the upper body of the subject P in the two-step normalized average gait are obtained.

$$\theta x\_dot2(\tau)=\theta x\_dot2\_with\_offset(\tau)-\theta x\_dot2\_ave \quad (6a)$$

$$\theta y\_dot2(\tau)=\theta y\_dot2\_with\_offset(\tau)-\theta y\_dot2\_ave \quad (6b)$$

Subsequently, in STEP9, the data acquisition device 10 calculates the estimated values of the angular velocities (the angular velocity in the roll direction θx_dot(τ) and the angular velocity in the pitch direction θy_dot(τ)) of the upper body of the subject P at each time τ of the two-step normalized average gait.

In this case, the estimated values of θx_dot(τ) and θy_dot(τ) are calculated as follows. First, as indicated by expressions (7a) and (7b) given below, the estimated value of the angular acceleration in the roll direction θx_dot2(τ) and the estimated value of the angular acceleration in the pitch direction θy_dot2(τ) are individually integrated to calculate the value of the angular velocity in the roll direction at each time τ, θx_dot_with_offset(τ), and the value of the angular velocity in the pitch direction at each time τ, θy_dot_with_offset(τ), in the case where it is assumed that the values of the angular velocities at initial time (τ=0) of the two-step normalized average gait (initial values being θx_dot(0) and θy_dot(0)) are zero.

$$\theta x\_dot\_with\_offset(\tau)=((ave\_period\_R+ave\_period\_L)/Tnorm)*\int_0^\tau(\theta x\_dot2(\tau))d\tau \quad (7a)$$

$$\theta y\_dot\_with\_offset(\tau)=((ave\_period\_R+ave\_period\_L)/Tnorm)*\int_0^\tau(\theta y\_dot2(\tau))d\tau \quad (7b)$$

Here, the average value of the angular velocity of the upper body in the period of the two-step gait of normal straight-ahead walking of a person generally becomes zero or substantially zero. Therefore, according to the present embodiment, the data acquisition device 10 determines the initial values θx_dot(0) and θy_dot(0) of the angular velocity in the roll direction θx_dot(τ) and the angular velocity in the pitch direction θy_dot(τ), respectively, such that the average values of the angular velocity in the roll direction θx_dot(τ) and the angular velocity in the pitch direction θy_dot(τ) in the two-step normalized average gait become zero.

Specifically, θx_dot(0) and θy_dot(0) are calculated according to the following expressions (8a) and (8b), respectively.

$$\theta x\_dot(0) = -\theta x\_dot\_ave \quad (8a)$$
$$= -(1/Tnorm)*\int_0^{Tnorm}(\theta x\_dot\_with\_offset(\tau))d\tau$$

$$\theta y\_dot(0) = -\theta y\_dot\_ave \quad (8b)$$
$$= -(1/Tnorm)*\int_0^{Tnorm}(\theta y\_dot\_with\_offset(\tau))d\tau$$

In other words, the value of the reverse polarity of the average value θx_dot_ave of θx_dot_with_offset(τ) and the value of the reverse polarity of the average value θy_dot_ave of θy_dot_with_offset(τ) in the two-step normalized average gait are calculated as θx_dot(0) and θy_dot(0), respectively.

Then, as indicated by expressions (9a) and (9b) given below, the data acquisition device 10 calculates a value, which is obtained by adding the foregoing initial value θx_dot(0) to θx_dot_with_offset(τ), and a value, which is obtained by adding the foregoing initial value θy_dot(0) to θy_dot_with_offset(τ), as the estimated value of the angular velocity in the roll direction θx_dot(τ) at each time τ and the estimated value of the angular velocity in the pitch direction θy_dot(τ) at each time τ, respectively. Thus, the waveform data of the estimated values of the angular velocities θx_dot (τ) and θy_dot(τ) of the upper body of the subject P in the two-step normalized average gait is obtained.

$$\theta x\_dot(\tau)=\theta x\_dot\_with\_offset(\tau)+\theta x\_dot(0) \quad (9a)$$

$$\theta y\_dot(\tau)=\theta y\_dot\_with\_offset(\tau)+\theta y\_dot(0) \quad (9b)$$

Subsequently, in STEP10, the data acquisition device 10 calculates the estimated values of the posture of the upper body of the subject P (the tilt angle in the roll direction θx(τ) and the tilt angle in the pitch direction θy(τ)) at each time of the two-step normalized average gait.

In this case, the estimated values of θx(τ) and θy(τ) are calculated as follows. First, as indicated by expressions (10a) and (10b) given below, the estimated value of the angular velocity in the roll direction θx_dot(τ) and the estimated value of the angular velocity in the pitch direction θy_dot(τ) are individually integrated to calculate the value of the tilt angle in the roll direction at each time τ, θx_with_offset(τ), and the value of the tilt angle in the pitch direction at each time τ, θy_with_offset(τ), in the case where it is assumed that the values of the tilt angles at initial time (τ=0) of the two-step normalized average gait (initial values being θx(0) and θy(0)) are zero.

$$\theta x\_with\_offset(\tau)=((ave\_period\_R+ave\_period\_L)/Tnorm)*\int_0^\tau (\theta x\_dot(\tau))d\tau \quad (10a)$$

$$\theta y\_with\_offset(\tau)=((ave\_period\_R+ave\_period\_L)/Tnorm)*\int_0^\tau (\theta y\_dot(\tau))d\tau \quad (10b)$$

Here, the average value of the tilt angle in the roll direction θx(τ) of the upper body of the subject P in the two-step normalized average gait is considered to coincide or substantially coincide with the difference between the average value of an actual tilt angle in the roll direction of the attitude of the first sensor unit 2 in the foregoing 2n gait (the sensor unit 2 in the vicinity of the base of neck) (the average value will be hereinafter denoted by θx_neck_ave) and an actual tilt angle in the roll direction of the first sensor unit 2 in the upright posture of the subject P (hereinafter denoted by θx_neck_up_right), the difference being hereinafter denoted by θx_neck_offset.

Similarly, the average value of the tilt angle in the pitch direction θy(τ) of the upper body of the subject P in the two-step normalized average gait is considered to coincide or substantially coincide with the difference between the average value of an actual tilt angle in the pitch direction of the attitude of the first sensor unit 2 in the foregoing 2n gait (the sensor unit 2 in the vicinity of the base of neck) (the average value will be hereinafter denoted by θy_neck_ave) and the estimated value of an actual tilt angle in the pitch direction of the first sensor unit 2 in the upright posture of the subject P (hereinafter denoted by θy_neck_up_right), the difference being hereinafter denoted by θy_neck_offset.

Therefore, according to the present embodiment, the data acquisition device 10 determines the initial values θx(0) and θy(0) of the tilt angle in the roll direction θx(τ) and the tilt angle in the pitch direction θy(τ), respectively, such that the average value of the tilt angle in the roll direction θx(τ) of the upper body of the subject P and the average value of the tilt angle in the pitch direction θy(τ) in the two-step normalized average gait coincide with the estimated value of the foregoing θx_neck_offset and the estimated value of the foregoing θy_neck_offset, respectively.

Specifically, the estimated value of θx_neck_offset and the estimated value of θy_neck_offset are calculated according to the following expressions (11a) and (11b), respectively.

$$\theta x\_neck\_offset=\theta x\_neck\_ave-\theta x\_neck\_up\_right \quad (11a)$$

$$\theta y\_neck\_offset=\theta y\_neck\_ave-\theta y\_neck\_up\_right \quad (11b)$$

Here, θx_neck_ave and θy_neck_ave are calculated from the value of the tilt angle in the roll direction and the value of the tilt angle in the pitch direction, respectively, in the attitude of the first sensor unit 2 sequentially estimated as described above by the arithmetic processing section 7 of the first sensor unit 2. Further, θx_neck_up_right and θy_neck_up_right denote values which have been measured beforehand when the subject P is in the upright posture and which have been stored and retained in the data acquisition device 10.

Further, the average values θx_ave and θy_ave of θx_with_offset(τ) and θy_with_offset(τ), respectively, which have been calculated according to the foregoing expressions (10a) and (10b), respectively, on the two-step normalized average gait, are calculated according to expressions (12a) and (12b) given below.

$$\theta x\_ave=(1/Tnorm)*\int_0^{Tnorm}(\theta x\_with\_offset(\tau))d\tau \quad (12a)$$

$$\theta y\_ave=(1/Tnorm)*\int_0^{Tnorm}(\theta y\_with\_offset(\tau))d\tau \quad (12b)$$

Further, as indicated by expression (13a) given below, the value of the reverse polarity of the difference between the foregoing calculated value of θx_ave and the foregoing calculated value of θx_neck_offset is calculated as θx(0). Further, as indicated by expression (13b) given below, the value of the reverse polarity of the difference between the foregoing calculated value of θy_ave and the foregoing calculated value of θy_neck_offset is calculated as θy(0).

$$\theta x(0)=-(\theta x\_ave-\theta x\_neck\_offset) \quad (13a)$$

$$\theta y(0)=-(\theta y\_ave-\theta y\_neck\_offset) \quad (13b)$$

Then, as indicated by expressions (14a) and (14b) given below, the data acquisition device 10 calculates the value obtained by adding the initial value θx(0) to θx_with_offset (τ) and the value obtained by adding the initial value θy(0) to θy_with_offset(τ) as the estimated value of the tilt angle in the roll direction at each time θx(τ) and the estimated value of the tilt angle in the pitch direction at each time θy(τ), respectively. Thus, the waveform data of the estimated values of the tilt angles θx(τ) and θy(τ) of the upper body of the subject P in the two-step normalized average gait is obtained.

$$\theta x(\tau)=\theta x\_with\_offset(\tau)+\theta x(0) \quad (14a)$$

$$\theta y(\tau)=\theta y\_with\_offset(\tau)+\theta y(0) \quad (14b)$$

Supplementarily, according to the present embodiment, the processing in STEP7 to STEP10 described above corresponds to the processing carried out by the upper body posture motion estimating unit 12 having the functions as the upper body angular acceleration estimating unit and the upper body angular velocity estimating unit in the present invention. In this case, the processing in STEP7 and STEP8 corresponds to the processing by the upper body angular acceleration estimating unit and the processing in STEP9 corresponds to the processing by the upper body angular velocity estimating unit.

According to the present embodiment, as described above, the waveform data of the estimated values of the angular acceleration θx_dot2(τ), the angular velocity θx_dot(τ) and the tilt angle θx(τ) in the roll direction of the upper body of the subject P and the waveform data of the estimated values of the angular acceleration θy_dot2(τ), the angular velocity θy_dot(τ) and the tilt angle θy(τ) in the pitch direction thereof are obtained as the data representatively indicating an actual change in the posture of the upper body.

Then, the data acquisition device 10 visually displays, on the display 10a thereof, the foregoing waveform data or the ratio between the normalization R support gait period norm_period_R and the normalization L support gait period norm_period_L (the average ratio between the R support gait period period_R and the L support gait period period_L) or the like. The display of the waveform data or the like may be replaced by printing.

FIG. 6 illustrates an example of the waveform data or the like displayed on the display 10a. The illustrated example includes a waveform graph of the angular acceleration of the upper body and a graph that visually displays the magnitudes of the normalization R support gait period norm_period_R and the normalization L support gait period norm_period_L.

The waveform of the graph can be switched to a waveform illustrating other than angular acceleration (e.g. the waveform of angular velocity or tilt angle).

The waveform data output from the data acquisition device 10 is not limited to the waveform data of the angular acceleration, the angular velocity or the posture (the tilt angle) of the upper body and may include the waveform data of acceleration of one of the sensor units 2 (e.g. the sensor unit 2 attached to the upper body of the subject P at a location in the vicinity of the waist) observed in the global coordinate system.

According to the upper body motion measurement system 1 of the present embodiment, the waveform data of the angular acceleration and the like of the upper body during a walking motion of the subject P is obtained as described above. Then, the waveform data can be used to analyze or assess the walking state of the subject P.

For example, in a walking motion of a physically unimpaired subject P, the motion of the upper body in the R support gait and the motion of the upper body in the L support gait are generally well balanced.

According to the present embodiment, the balance between the R support gait and the L support gait in the walking motion of the subject P can be assessed from the ratio (or the magnitude relationship) between the normalization R support gait period norm_period_R and the normalization L support gait period norm_period_L, or from the waveform of the angular acceleration, the angular velocity or the tilt angle of the upper body in each of the normalization R support gait period norm_period_R and the normalization L support gait period norm_period_L.

Thus, it can be assessed, for example, whether one of the legs of the subject P has a problem or how much the leg having the problem has recovered.

Figure 7A:
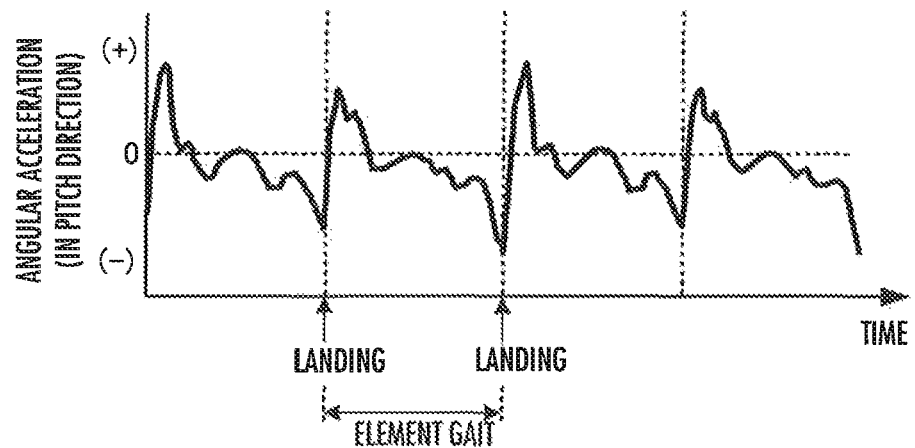
FIG. 7A and FIG. 7B are graphs for explaining an example of the processing for assessing data obtained in the embodiment.

Further, during the walking motion of the physically unimpaired subject P, the posture of the upper body, in general, automatically (unconsciously) moves in the pitch direction so as to generate angular acceleration in the direction that causes the upper body to lean backward (angular acceleration in the negative direction about the Y-axis) immediately before a leg lands, as illustrated in FIG. 7A. As a result, the change in the posture of the upper body balances with the angular acceleration in the pitch direction of the upper body attributable to a landing impact (angular acceleration in the positive direction about the Y-axis). This leads to smooth transition to the next walking cycle.

Figure 7B:
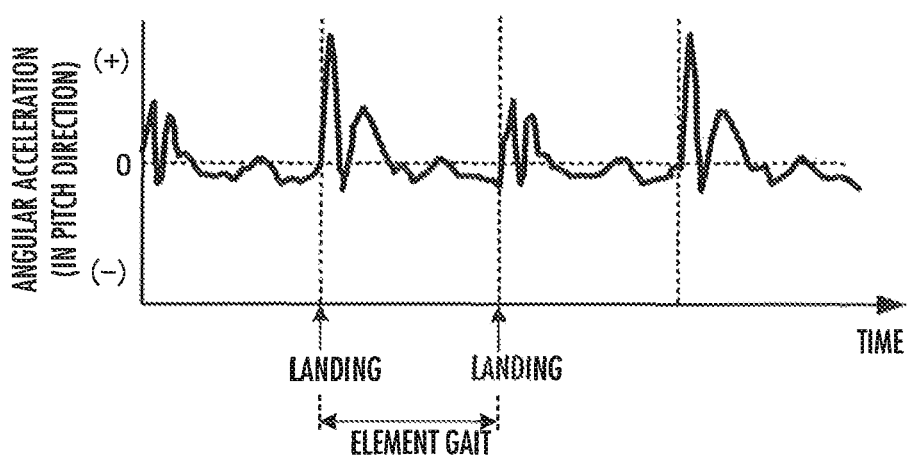

Meanwhile, in a walking motion of the subject P having a problem with his/her leg, there are some cases where a force for coping with a landing impact cannot be fully generated, and the angular acceleration in the pitch direction of the upper body exhibits a waveform that spikes in the positive direction about the Y-axis immediately after a leg lands, as illustrated in FIG. 7B.

Therefore, the state of the problem of the subject P can be assessed by observing the waveform of the angular acceleration in the pitch direction of the upper body in the vicinity of the landing point of each leg of the subject P.

Second Embodiment

A second embodiment of the present invention will now be described with reference primarily to FIG. 8A and FIG. 8B. An upper body motion measurement system of the present embodiment differs from the upper body motion measurement system 1 of the first embodiment described above only in the layout of the sensor units and a part of the processing carried out by the data acquisition device. The description of the present embodiment, therefore, will be focused mainly on the aspects that are different from the first embodiment. Further, the description of the aspects that are the same as those of the first embodiment will be omitted.

Figure 8A:
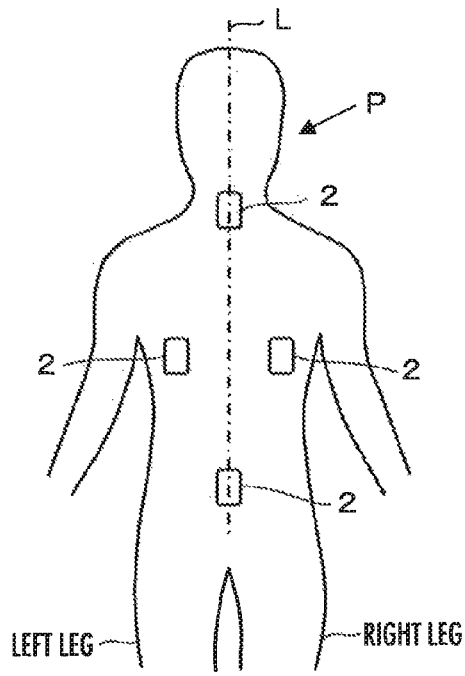
FIG. 8A and FIG. 8B are diagrams illustrating examples of the layout of the inertia sensor units attached to the upper body of the subject in a second embodiment.

Referring to FIG. 8A, a measurement system according to the present embodiment has four sensor units (inertial sensor units) 2, 2, 2, 2. The configuration of each of the sensor units 2 is the same as that in the first embodiment.

Of the four sensor units 2, 2, 2, 2, two sensor units 2, 2 are attached to a place in the vicinity of the base of the neck and a place in the vicinity of the waist of a subject P on a line along a spine of the back of the upper body (on a line along the body trunk axis) of the subject P, as with the first embodiment. Hereinafter, as with the first embodiment, the upper sensor unit 2 (in the vicinity of the base of the neck) of the two sensor units 2, 2 will be referred to as the first sensor unit 2 and the lower sensor unit 2 (in the vicinity of the waist) will be referred to as the second sensor unit 2 in some cases.

Further, the remaining two sensor units 2, 2 are attached to the back (dorsal surface) of the upper body, namely, at a place on the left side and at a place on the right side of the spine (body trunk axis) of the upper body of a person. The attaching places are positioned at the same height on the upper body such that the places are laterally symmetrical relative to the spine of the upper body of the person. The height positions may be, for example, the positions in the vicinity of the chest of the subject P as illustrated in FIG. 8A, or the positions that are approximately level with the shoulders of the subject P as illustrated in FIG. 8B.

Hereinafter, one of the two sensor units 2, 2 disposed at the place on the left side and at the place on the right side of the upper body of the subject P as described above, e.g. the sensor unit 2 on the left side, will be referred to as a third sensor unit 2 and the other sensor unit 2 (on the right side) will be referred to as a fourth sensor unit 2 in some cases. Further, any one of the first to the fourth sensor units 2 will be referred to as an i-th sensor unit 2 (i=1, 2, 3 or 4) in some cases.

The configuration of the upper body motion measurement system of the present embodiment is the same as that of the first embodiment except for the aspects described above.

The description will now be given of the measurement processing carried out by the upper body motion measurement system according to the present embodiment.

As with the first embodiment, the measurement data transmitted from each of the sensor units 2 (the measurement data indicating the estimated value of the attitude and the detection value of the acceleration vector of each of the sensor units 2 at each time while the subject P is walking) to a data acquisition device 10 is stored and retained in a time series manner in a storage medium of the data acquisition device 10.

Further, the data acquisition device 10 uses the measurement data to carry out processing for analyzing the motion of the upper body of the subject P according to the flowchart given in FIG. 4, as with the first embodiment.

According to the present embodiment, however, the processing in STEP2 and STEP4 is carried out on each of the four sensor units 2.

Further, according to the present embodiment, in the processing from STEP7, the processing for estimating the angular acceleration, the angular velocity and the rotational angle in a yaw direction (Z-axis direction) of the upper body of the subject P is added to the processing described in the first embodiment.

Specifically, the data acquisition device 10 calculates, in STEP7, angular acceleration in the yaw direction (the direction about the Z-axis) θz_dot2_with_offset in addition to angular acceleration in the roll direction (the direction about an X-axis) θx_dot2_with_offset and angular acceleration in the pitch direction (the direction about a Y-axis) θy_dot2_with_offset of the upper body of the subject P.

In this case, the data acquisition device 10 calculates the angular acceleration in the yaw direction (the direction about the Z-axis) θz_dot2_with_offset of the upper body of the subject P by the linear combination indicated in expression (4c) below from an X-axis direction component norm_ave_acc_1_x_global of a normalized third average acceleration vector norm_ave_acc_3_global of the third sensor unit 2 (the sensor unit 2 on the right side) and an X-axis direction component norm_ave_acc_4_x_global of a normalized fourth average acceleration vector ↑norm_ave_acc_4_global of the fourth sensor unit 2 (the sensor unit 2 on the left side).

$$\theta z\_dot2\_with\_offset(\tau)=(norm\_ave\_acc\_3\_x\_global(\tau)-norm\_ave\_acc\_4\_x\_global(\tau))/\Delta y \quad (4c)$$

where

Δy: Distance in the Y-axis direction (lateral direction) between the third sensor unit 2 and the fourth sensor unit 2

The value of Δy of expression (4c) given above uses a value measured beforehand (fixed value) of the distance in the Y-axis direction between the third sensor unit 2 and the fourth sensor unit 2 in a state in which the subject P is standing upright.

Further, in the next STEP8, the data acquisition device 10 carries out processing for eliminating an offset component from the calculated value of the angular acceleration in the yaw direction θz_dot2_with_offset in addition to removing the offset components from the calculated values of the angular acceleration in the roll direction θx_dot2_with_offset and the angular acceleration in the pitch direction θy_dot2_with_offset.

In the processing, the data acquisition device 10 calculates an average value θz_dot2_ave of the angular acceleration in the yaw direction θz_dot2_with_offset of the upper body of the subject P in the foregoing two-step normalized average gait according to expression (5c) given below.

$$\theta z\_dot2\_ave=(1/Tnorm)*\int_0^{Tnorm}(\theta z\_dot2\_with\_offset(\tau))d\tau \quad (5c)$$

Then, according to expression (6c) given below, the data acquisition device 10 calculates a value, which is obtained by subtracting the average value θz_dot2_ave (offset component) calculated as described above from the angular acceleration in the yaw direction at each time τ, θz_dot2_with_offset(τ), in the two-step normalized average gait, as the estimated value of an actual angular acceleration in the yaw direction θz_dot2(τ) of the upper body of the subject P. Thus, more waveform data of the estimated value of the angular acceleration in the yaw direction θz_dot2(τ) of the upper body of the subject P in the two-step normalized average gait is obtained.

$$\theta z\_dot2(\tau)=\theta z\_dot2\_with\_offset(\tau)-\theta z\_dot2\_ave \quad (6c)$$

Further, in the next STEP9, the data acquisition device 10 calculates the estimated value of the angular velocity in the yaw direction θz_dot(τ) in addition to the estimated values of the angular velocity in the roll direction θx_dot(τ) and the angular velocity in the pitch direction θy_dot(τ) of the upper body of the subject P at each time τ of the two-step normalized average gait.

In this case, the estimated value of θz_dot(τ) is calculated as follows. First, according to expression (7c) given below, the estimated value of the angular acceleration in the yaw direction θz_dot2(τ) is integrated so as to calculate the value of the angular velocity in the yaw direction at each time τ, θz_dot_with_offset(τ), in the case where the value of the angular velocity at initial time (τ=0) of the two-step normalized average gait (initial value θz_dot(0)) is assumed zero.

$$\theta z\_dot\_with\_offset(\tau)=((ave\_period\_R+ave\_period\_L)/Tnorm)*\int_0^{\tau}(\theta z\_dot2(\tau))d\tau \quad (7c)$$

Here, as described above, the average value of the angular velocity of the upper body in the period of the two-step gait of normal straight-ahead walking of a person generally becomes zero or substantially zero. Therefore, the data acquisition device 10 determines an initial value θz_dot(0) of the angular velocity in the yaw direction θz_dot(τ) such that the average value of the angular velocity in the yaw direction θz_dot(τ) in the two-step normalized average gait become zero.

Specifically, θz_dot(0) is calculated according to expression (8c) given below.

$$\theta z\_dot(0) = -\theta z\_dot\_ave \quad (8c)$$
$$= -(1/Tnorm)*\int_0^{Tnorm}(\theta z\_dot\_with\_offset(\tau))d\tau$$

In other words, the value of the reverse polarity of the average value θz_dot_ave of θz_dot_with_offset(τ) in the two-step normalized average gait is calculated as θz_dot(0).

Further, according to expression (9c) given below, the data acquisition device 10 calculates the value, which is obtained by adding the foregoing initial value θz_dot(0) to θz_dot_with_offset(τ), as the estimated value of the angular velocity in the yaw direction at each time τ, θz_dot(τ). Thus, more waveform data of the estimated value of the angular velocity in the yaw direction θz_dot(τ) of the upper body of the subject P in the two-step normalized average gait is obtained.

$$\theta z\_dot(\tau)=\theta z\_dot\_with\_offset(\tau)+\theta z\_dot(0) \quad (9c)$$

In the next STEP10, the data acquisition device 10 calculates the estimated value of the rotational angle in the yaw direction θz(τ) in addition to the estimated values of the tilt angle in the roll direction θx(τ) and the tilt angle in the pitch direction θy(τ) of the upper body of the subject P at each time of the two-step normalized average gait.

In this case, the estimated value of θz(τ) is calculated as follows. First, according to expression (10c) given below, the estimated value of the angular velocity in the yaw direction θz_dot(τ) is integrated so as to calculate the value of the rotational angle in the yaw direction at each time τ, θz_with_offset(τ), in the case where the value of the rotational angle at initial time (τ=0) of the two-step normalized average gait (initial value θz(0)) is assumed zero.

$$\theta z\_with\_offset(\tau)=((ave\_period\_R+ave\_period\_L)/Tnorm)*\int_0^\tau (\theta z\_dot(\tau))d\tau \quad (10c)$$

Here, the average value of the rotational angle in the yaw direction θx(τ) of the upper body of the subject P in the two-step normalized average gait generally becomes zero or substantially zero.

According to the present embodiment, therefore, the data acquisition device 10 determines an initial value θz(0) of the rotational angle in the yaw direction θz(τ) such that the average value of the rotational angle in the yaw direction θz(τ) of the upper body of the subject P in the two-step normalized average gait becomes zero.

Specifically, according to expression (13c) given below, the value of the reverse polarity of the average value θz_ave of θz_with_offset(τ), which has been calculated according to the foregoing expression (10c) for the two-step normalized average gait, is calculated as θz(0).

$$\theta z(0) = -\theta z\_ave \quad (13c)$$
$$= -(1/Tnorm)*\int_0^{Tnorm}(\theta z\_with\_offset(\tau))d\tau$$

Further, according to expression (14c) given below, the data acquisition device 10 calculates the value, which is obtained by adding the foregoing initial value θz(0) to θz_with_offset(τ), as the estimated value of the rotational angle in the yaw direction at each time τ, θz(τ). Thus, more waveform data of the estimated value of the rotational angle in the yaw direction θz(τ) of the upper body of the subject P in the two-step normalized average gait is obtained.

$$\theta z(\tau)=\theta z\_with\_offset(\tau)+\theta z(0) \quad (14c)$$

The present embodiment is the same as the first embodiment except for the aspects described above.

According to the present embodiment, the angular accelerations, the angular velocities and the tilt angles in the roll direction and the pitch direction of the upper body and also the estimated values of the angular acceleration, the angular velocity and the rotational angle in the yaw direction, and the waveform data thereof can be used to analyze or assess the walking state of the subject P.

[Modifications]

Some modifications related to the embodiments described above will now be described.

In the foregoing embodiments, the estimated values of the angular acceleration of the upper body of the subject P have been calculated according to the foregoing expressions (4a), (4b) and (4c). However, if, for example, the upper body tilts from an upright posture into the roll direction, then the translational acceleration vectors of the sensor units 2 (especially the sensor unit 2 on the upper side of the upper body) will change in the Y-axis direction component and also the Z-axis direction component according to a change in the angular acceleration in the roll direction of the upper body.

Similarly, if, for example, the upper body tilts from an upright posture into the pitch direction, then the translational acceleration vectors of the sensor units 2 (especially the sensor unit 2 on the upper side of the upper body) will change in the X-axis direction component and also the Z-axis direction component according to a change in the angular acceleration in the pitch direction of the upper body.

Considering the above, the estimated values of the angular accelerations of the upper body in the directions, namely, the roll direction, the pitch direction and the yaw direction, can be more generally calculated by linearly combining the accelerations of the plurality of sensor units 2 attached to the upper body.

For example, in the processing in the foregoing STEP7, it is possible to calculate the estimated values (the estimated values before the offset components are removed) of the angular acceleration of the upper body in the directions, namely, the roll direction, the pitch direction, and the yaw direction, according to expressions (15a), (15b) and (15c) given below.

$$\theta x\_dot2\_with\_offset(\tau)=\sum_{i=1}^N w\_xy\_i*norm\_ave\_acc\_i\_y\_global(\tau)+\sum_{i=1}^N w\_xz\_i*norm\_ave\_acc\_2\_y\_global(\tau) \quad (15a)$$

$$\theta y\_dot2\_with\_offset(\tau)=\sum_{i=1}^N w\_yx\_i*norm\_ave\_acc\_i\_x\_global(\tau)+\sum_{i=1}^N w\_yz\_i*norm\_ave\_acc\_2\_z\_global(\tau) \quad (15b)$$

$$\theta z\_dot2\_with\_offset(\tau)=\sum_{i=1}^N w\_zx\_i*norm\_ave\_acc\_i\_x\_global(\tau)+\sum_{i=1}^N w\_zy\_i*norm\_ave\_acc\_2\_y\_global(\tau) \quad (15c)$$

N denotes the quantity of the sensor units 2 attached to the upper body, and w_xy_i, w_xz_i, w_yx_i, w_yz_i, w_zx_i, and w_zy_i (i=1, 2, . . . , N) denote weight coefficients. The values of the weight coefficients w_xy_i, w_xz_i, w_yx_i, w_yz_i, w_zx_i, and w_zy_i can be set beforehand based on experiments or the like. In this case, some of the weight coefficients w_xy_i, w_xz_i, w_yx_i, w_yz_i, w_zx_i, and w_zy_i may be zero.

Calculating the estimated value of the angular acceleration of the upper body as described above makes it possible to enhance the reliability of the estimated value of the angular acceleration.

Figure 8B:
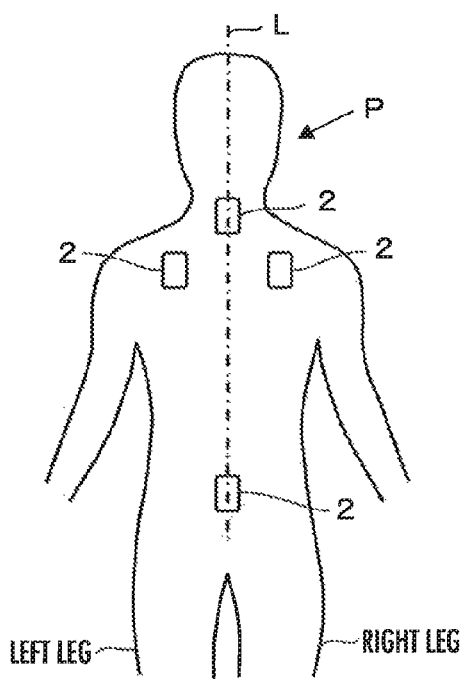

Further, in the foregoing embodiments, the plurality of sensor units 2 attached to the upper body has been laid out as illustrated in FIG. 1B, FIG. 8A or FIG. 8B. Alternatively, however, the layout illustrated in, for example, FIG. 9 may be adopted as the layout of the sensor units 2. In this example, one of the three sensor units 2 is attached to the upper body at the height in the vicinity of the waist of the subject P. Further, the two sensor units 2 are attached to the upper body so as to be laterally symmetrical relative to a body trunk L at the upper portion of the upper body (e.g. a portion at the height in the vicinity of the shoulders).

Further, in the foregoing embodiments, the sensor units 2 have been attached to the back (dorsal surface) of the upper body. Alternatively, however, the sensor units 2 may be attached to the front side (abdominal side) of the upper body.

Further, in the foregoing embodiments, the waveform of each component of the normalized i-th average acceleration vector ↑norm_ave_acc_i_global has been calculated and then the estimated value of the angular acceleration of the upper body in the two-step normalized average gait has been calculated. Alternatively, however, the time series of the estimated value of the angular acceleration in each direction of the upper body in the entire 2n gait can be calculated by carrying out the same calculation as expressions (4a), (4b) and (4c) or expressions (15a), (15b) and (15c), directly using the values of the components of the i-th global acceleration vector ↑acc_i_global calculated in the foregoing STEP2 in place of the components of the normalized i-th average acceleration vector ↑norm_ave_acc_i_global.

In this case, the average waveform data of the angular acceleration in each direction can be generated by normalizing and averaging the waveform of the estimated value of the angular acceleration calculated as described above by the same processing as that for normalizing and averaging the waveform of each component of the i-th global acceleration vector ↑acc_i_global.

In this case, after generating the average waveform data of the angular acceleration of the upper body, the estimated value of the angular acceleration, from which an offset component has been removed, can be calculated, the angular velocity can be calculated, and the estimated value of the posture (the tilt angle or the rotational angle) of the upper body can be calculated by carrying out the same processing as that in the foregoing STEP8 to STEP10.

Further, in the foregoing embodiments, the same processing as that in the foregoing STEP8 may be carried out on the waveform data (average waveform data) of each component of the normalized i-th average acceleration vector ↑norm_ave_acc_i_global, which has been generated in STEP6, thereby to carry out the processing for removing an offset component.

More specifically, the average value of each component of ↑norm_ave_acc_i_global in the period of the two-step normalized average gait is determined as the offset component. Further, the offset component is subtracted from the value of the component thereby to determine the average waveform data free from the offset component. In this case, the processing in the foregoing STEP8 may be omitted.

Further, in the foregoing embodiments, the ground contact sensors 21, 21 have been used to recognize, by the data acquisition device 10, the timing of switching from the R support gait to the L support gait or vice versa. Alternatively, however, the timing of the switching can be recognized based on the detection value of the acceleration in a predetermined direction indicated by a detection output of the acceleration sensor 5 of any one of the sensor units 2 attached to the upper body of the subject P (the acceleration of the sensor unit 2 observed in the sensor unit local coordinate system Cs) or a change in a predetermined direction component of the i-th global acceleration vector on any one of the sensor units 2.

Figure 10:
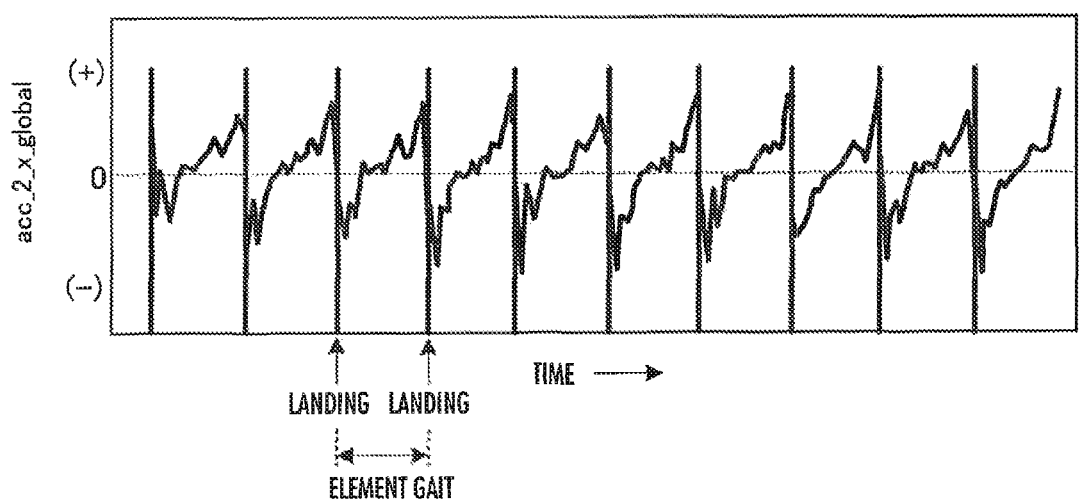
FIG. 10 is a graph for explaining a modification according to the embodiments of the present invention.

For example, the estimated value of the X-axis direction component acc_2_x_global of a second global acceleration vector ↑acc_2_global on the sensor unit 2 attached to the vicinity of the waist of the subject P (the second sensor unit 2) suddenly changes to acceleration in a decelerating direction (the negative direction of the X-axis) at the instant a free leg in each element gait lands, as illustrated in FIG. 10, in a walking motion of the subject P. The same applies to an X-axis direction component acc_2_x_local of the detection value of a second local acceleration vector ↑acc_2_local on the second sensor unit 2.

Hence, the differential value (temporal change rate) of the X-axis direction component acc_2_x_global of ↑acc_2_global or the differential value (temporal change rate) of the X-axis direction component acc_2_x_local of ↑acc_2_x_local is sequentially calculated. Then, the timing at which the differential value is a negative value (a value in a direction in which the second sensor unit 2 decelerates in the X-axis direction) and the absolute value or the square value thereof reaches a predetermined set threshold value or more may be recognized as the timing at which the R support gait is switched to the L support gait or vice versa.

Further, in the case where the timing at which the R support gait is switched to the L support gait or vice versa is recognized, whether the right leg or the left leg is the supporting leg in each element gait can be recognized according to, for example, a change pattern of the Y-axis direction component acc_2_y_global of the second global acceleration vector ↑acc_2_global on the second sensor unit 2.

Figure 11:
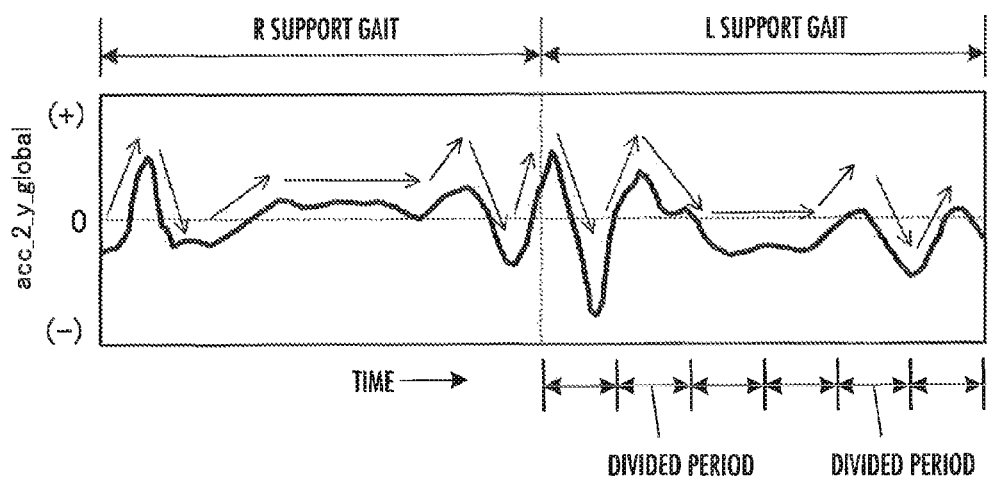
FIG. 11 is a graph for explaining another modification according to the embodiments of the present invention.

More specifically, as illustrated in FIG. 11, the waveform of the Y-axis direction component acc_2_y_global of ↑acc_2_global has a characteristic change pattern for each of the R support gait and the L support gait. Therefore, it is possible to recognize whether the supporting leg is the right leg or the left leg in each element gait according to the characteristic of the change pattern.

In this case, the change pattern of the waveform of acc_2_y_global can be recognized by, for example, the following technique. As illustrated in FIG. 11, the period of each element gait is divided into a plurality of periods.

Then, for each divided period, the change pattern of acc_2_y_global in each divided period is categorized according to the amount of a change from the start to the end of the divided period acc_2_y_global (the difference between the value at the end and the value at the start) and the polarity of acc_2_y_global in the divided period (specifically, the polarity corresponding to the duration of the positive polarity in the divided period or the duration of the negative polarity therein, whichever is longer).

Then, the change patterns in all the divided periods of each element gait are checked against change patterns set beforehand that correspond to the R support gait and the L support gait for the degree of coincidence, thus making it possible to recognize whether the supporting leg in each element gait is the right leg or the left leg.

Further, for example, in place of the foregoing ground contact sensors 21, acceleration sensors may be attached to the feet of the subject P. In this case, the absolute value of the acceleration detected by the acceleration sensor attached to each foot suddenly becomes large at the instant a leg lands on or leaves from a floor. This makes it possible to recognize the timing at which a leg lands on or leaves from a floor, which is detected based on a change in the absolute value of the acceleration, as the timing of the switching between the R support gait and the L support gait.

What is claimed is:

1. An upper body motion measurement system comprising:
   at least one central processing unit comprising
   a plurality of inertia sensor units, each of which includes
      a set of an angular velocity sensor that detects an angular velocity and an acceleration sensor that detects an acceleration and which are attached to places that are different from each other on an upper body of a subject;
   a sensor unit attitude estimating unit configured to estimate an attitude of each of the inertia sensor units in a motion environment of the subject based on a detection value of an angular velocity and a detection value of an acceleration indicated by detection outputs of the angular velocity sensor and the acceleration sensor of each of the inertia sensor units attached to the upper body of the subject;

a sensor unit acceleration estimating unit configured to estimate an acceleration of each of the inertia sensor units observed in a global coordinate system set in the motion environment of the subject based on a detection value of an acceleration indicated by a detection output of the acceleration sensor of each of the inertia sensor units attached to the upper body of the subject, and the attitude of each of the inertia sensor units estimated by the sensor unit attitude estimating unit; and an upper body angular acceleration estimating unit configured to estimate an angular acceleration of the upper body of the subject observed in the global coordinate system based on a set of accelerations estimated by the sensor unit acceleration estimating unit on each of the plurality of the inertia sensor units.

2. The upper body motion measurement system according to claim 1, wherein the plurality of the inertia sensor units includes at least two inertia sensor units attached to the upper body with an interval provided in a vertical direction of the upper body along a trunk axis of the subject, and the angular acceleration estimated by the upper body angular acceleration estimating unit includes at least one of the angular acceleration of the upper body in a roll direction of the subject and the angular acceleration in a pitch direction of the subject.

3. The upper body motion measurement system according to claim 2, wherein an upper inertia sensor unit of the two inertia sensor units is attached to the upper body of the subject at a location on an upper side from a boundary between a thoracic vertebra and a lumbar vertebra of the subject, and a lower inertia sensor unit of the two inertia sensor units is attached to the upper body of the subject at a location on a lower side from the boundary between the thoracic vertebra and the lumbar vertebra of the subject.

4. The upper body motion measurement system according to claim 1, wherein the acceleration of each of the inertia sensor units observed in the global coordinate system or the angular acceleration of the upper body of the subject observed in the global coordinate system is defined as a target state amount, and the sensor unit acceleration estimating unit or the upper body angular acceleration estimating unit is configured to carry out basic estimated value generation processing for generating a time series of estimated values of the target state amount in a walking motion and average waveform data generation processing for generating average waveform data of the target state amount in a gait for two steps in the walking motion in a case where the subject wearing the plurality of the inertia sensor units on his/her upper body performs the walking motion, and the average waveform data generation processing is configured to transform in scale the waveform data, which is indicated by the time series of the estimated values of the target state amount generated by the basic estimated value generation processing for each of an n number (n: an integer of 2 or more) of two-step gaits included in the walking motion of the subject, in a direction of a time axis thereby to generate normalized waveform data obtained by normalizing a time width of a period of the two-step gait and further configured to generate average waveform data of an n number of pieces of the normalized waveform data for each of the n number of the two-step gaits as the average waveform data.

5. The upper body motion measurement system according to claim 4, wherein processing for generating the normalized waveform data in the average waveform data generation processing is configured to generate the normalized waveform data such that a ratio between a time width of a one-step period of a right leg of the subject and a time width of a one-step period of a left leg of the subject in the normalized waveform data coincides with a ratio between an average value of an actual time width of the one-step period of the right leg in an n number of two-step gaits included in the walking motion of the subject and an average value of an actual time width of the one-step period of the left leg in the n number of two-step gaits.

6. The upper body motion measurement system according to claim 4, wherein the sensor unit acceleration estimating unit or the upper body angular acceleration estimating unit, which carries out the average waveform data generation processing, is configured to further carry out offset component removal processing for removing an offset component from the average waveform data generated by the average waveform data generation processing, and the offset component removal processing is configured to remove the offset component such that a condition is satisfied, in which an average value in the period of the two-step gait of the value of the target state amount indicated by average waveform data after the offset component is removed becomes zero.

7. The upper body motion measurement system according to claim 4, wherein the sensor unit acceleration estimating unit or the upper body angular acceleration estimating unit, which carries out the average waveform data generation processing, is configured to recognize a switching timing for each step in a walking motion of the subject based on a detection value of acceleration indicated by a detection output of an acceleration sensor of at least one inertia sensor unit among the plurality of the inertia sensor units or a change in acceleration estimated by the sensor unit acceleration estimating unit on at least the one inertia sensor unit.

8. The upper body motion measurement system according to claim 4, wherein the sensor unit acceleration estimating unit is configured to generate the average waveform data related to the acceleration of each of the inertia sensor units, the upper body angular acceleration estimating unit is configured to generate angular acceleration waveform data composed of a time series of an estimated value of the angular acceleration of the upper body of the subject in the period of the two-step gait by using an estimated value of the acceleration of each of the inertia sensor units indicated by the average waveform data generated by the sensor unit acceleration estimating unit related to each of the plurality of inertia sensor units, an upper body angular velocity estimating unit that calculates an estimated value of the angular velocity of the upper body of the subject by integrating an estimated value of angular acceleration indicated by the angular acceleration waveform data generated by the upper body angular acceleration estimating unit is further provided, and the upper body angular velocity estimating unit is configured to calculate an estimated value of an angular velocity of the upper body of the subject such that a condition is satisfied, in which an average value of an estimated value of the angular velocity of the upper body of the subject in the period of the two-step gait is zero.

9. The upper body motion measurement system according to claim 4, wherein the upper body angular acceleration estimating unit is configured to generate the average waveform data related to the angular acceleration of the upper body of the subject, an upper body angular velocity estimating unit that calculates an estimated value of the angular velocity of the upper body of the subject by integrating an estimated value of angular acceleration indicated by the average waveform data generated by the upper body angular acceleration estimating unit is further provided, and the upper body angular velocity estimating unit is configured to calculate an estimated value of the angular velocity of the upper body of the subject such that a condition is satisfied, in which an average value of the estimated value of the angular velocity of the upper body of the subject in the period of the two-step gait is zero.

10. An upper body motion measurement method comprising:

a first step of acquiring a detection output of each of an angular velocity sensor and an acceleration sensor of each of a plurality of inertia sensor units in a state in which the plurality of the inertia sensor units, each of which has a set of the angular velocity sensor that detects an angular velocity and the acceleration sensor that detects an acceleration, is attached to places that are different from each other on an upper body of a subject;

a second step of estimating an attitude of each of the inertia sensor units in a motion environment of the subject based on a detection value of an angular velocity and a detection value of an acceleration indicated by detection outputs of the angular velocity sensor and the acceleration sensor of each of the inertia sensor units acquired in the first step;

a third step of estimating an acceleration of each of the inertia sensor units observed in a global coordinate system set in a travel environment of the subject based on a detection value of an acceleration indicated by a detection output of the acceleration sensor of each of the inertia sensor units acquired in the first step, and the attitude of each of the inertia sensor units estimated in the second step on each of the inertia sensor units; and a fourth step of estimating an angular acceleration of the upper body of the subject observed in the global coordinate system based on a set of accelerations estimated in the third step on each of the plurality of the inertia sensor units.

11. The upper body motion measurement system according to claim 1, wherein the angular velocity detected by the angular velocity sensor of each of the inertial sensor units is a three-dimensional space angular velocity vector, and wherein the acceleration detected by the acceleration sensor of each of the inertial sensor units is a three-dimensional space acceleration vector.

* * * * *